US008961999B2

(12) United States Patent
Davis et al.

(10) Patent No.: US 8,961,999 B2
(45) Date of Patent: Feb. 24, 2015

(54) METHODS AND COMPOSITIONS FOR BONE FORMATION

(75) Inventors: Alan R. Davis, Missouri City, TX (US); Elizabeth A. Davis, Missouri City, TX (US); Kevin Moran, The Woodlands, TX (US); Ronke Olabisi, Houston, TX (US); Jennifer L. West, Houston, TX (US); Christy Franco, Houston, TX (US)

(73) Assignees: Baylor College of Medicine, Houston, TX (US); William Marsh Rice University, Houston, TX (US)

( * ) Notice: Subject to any disclaimer, the term of this patent is extended or adjusted under 35 U.S.C. 154(b) by 0 days.

(21) Appl. No.: 13/513,086

(22) PCT Filed: Dec. 1, 2010

(86) PCT No.: PCT/US2010/058603
§ 371 (c)(1),
(2), (4) Date: Oct. 7, 2012

(87) PCT Pub. No.: WO2011/068903
PCT Pub. Date: Jun. 9, 2011

(65) Prior Publication Data
US 2013/0017228 A1 Jan. 17, 2013

Related U.S. Application Data

(60) Provisional application No. 61/392,109, filed on Oct. 12, 2010, provisional application No. 61/333,571, filed on May 11, 2010, provisional application No. 61/265,507, filed on Dec. 1, 2009.

(51) Int. Cl.
*A61K 35/12* (2006.01)
*A61P 19/00* (2006.01)
*A61K 9/50* (2006.01)
*C12N 5/00* (2006.01)
*A61K 9/00* (2006.01)
*C07K 14/51* (2006.01)
*C12N 5/077* (2010.01)

(52) U.S. Cl.
CPC ............ *C12N 5/0012* (2013.01); *A61K 9/0019* (2013.01); *A61K 9/5031* (2013.01); *C07K 14/51* (2013.01); *C12N 5/0652* (2013.01); *A61K 2035/128* (2013.01); *C12N 2510/02* (2013.01); *C12N 2533/30* (2013.01)
USPC ........................................ 424/400; 424/93.21

(58) Field of Classification Search
None
See application file for complete search history.

(56) References Cited

U.S. PATENT DOCUMENTS 6,939,557 B2 * 9/2005 Rowe et al. ................. 424/424

OTHER PUBLICATIONS

Bikram et al. "Endochondral bone formation from hydrogel carriers loaded with BMP-2 transduced cells" Annals Biomed Eng. 2007, 35 (5) pp. 796-807.*
Bikram et al. "Endochondral bone formation from hydrogel carriers loaded with BMP2-transduced cells" (2007).*
Yeh et al. "Micromolding of shape-controlled, harvestable cell-laden hydrogels" (2006).*
Bikram et al., "Endochondral bone formation from hydrogel carriers loaded with BMP-2 transduced cell". Ann Biomed Eng. 2007, 35 (5): pp. 796-80.
Yeh et al., "Micromolding of shape-controlled, harvestable cell-laden hydrogels", Biomaterials 2006, 7 (31): pp. 5391-5398.
Fouletier-Dilling et al., "Novel compound enable high-level adenovirus transduction in the absence of an adenovirus-specific receptor". Hum Gene Therapy 2005 16 (11): pp. 1287-1297.
Burdick et al., "Photoencapsulation of osteoblasts in injectable RGD-modified PEG hydrogels for bone tissue engineering", Biomaterials 2002, 23 (22) pp. 4315-4323.
Gobin et al., "Cell migration through defined, synthetic ECM analogs". FASEB J 2002, 16(7); pp. 751-752.
International Search Report and Written Opinion issued for PCT/US2010/058603, dated Apr. 14, 2011, 9 pages.
Olabisi, et al; Hydrogel Microshpere Encapsulation of a Cell-Based Gene Therapy System Increases Cell Survival of Injected Cells, Transgene Expression, and Bone Volume in a Model of Heterotopic Ossification; Tissue Engineering: Part A, vol. 16, No. 12; 2010.
Elizabeth A Olmested, et al; Adenovirus-Mediated BMP2 Expression in Human Bone Marrow Stromal Cells; Journal of Cellular Biochemistry 82:11-21 (2001).
ZaWauyka W. Lazard, et al.; Cell-Based Gene Gherapy for Repair of Critical Size Defects in the Rat Fibula; National Insitutes of Health, J Cell Biochem, Jun. 2011; 112(6): 1563-1571.

* cited by examiner

*Primary Examiner* — Robert A Wax
*Assistant Examiner* — Danah Al-Awadi
(74) *Attorney, Agent, or Firm* — Fulbright & Jaworski LLP

(57) ABSTRACT

A method and system to induce bone growth by locally delivering bone morphogenetic proteins (BMPs) to the target location for a prolonged period without invasive procedures are disclosed. The new bone growth is induced by delivering cells producing BMPs from transduced viral vectors to the target cite. In various embodiments, the cells are encapsulated in hydrogel microspheres that are non-degradable or degradable by enzymes produced during the bone formation process. Various embodiments may be used to induce spinal fusion or repair critical bone defects.

8 Claims, 14 Drawing Sheets

METHODS AND COMPOSITIONS FOR BONE FORMATION

CROSS-REFERENCE TO RELATED APPLICATIONS

This application is a national phase application under 35 U.S.C. §371 of International Application No. PCT/US2010/058603 filed Dec. 1, 2010 entitled "METHODS AND COMPOSITIONS FOR BONE FORMATION," which claims priority to U.S. Provisional Patent Application No. 61/265,507 filed Dec. 1, 2009 and entitled "HARNESSING HETEROTOPIC OSSIFICATION AS A RELIABLE NON-INVASIVE METHOD FOR SPINE FUSION;" U.S. Provisional Patent Application No. 61/333,571 filed May 11, 2010 and entitled "HYDROGEL MICROSPHERE ENCAPSULATION OF A CELL-BASED GENE THERAPY SYSTEM INCREASES CELL SURVIVAL, TRANSGENE EXPRESSION, AND BONE VOLUME IN A MODEL OF HETEROTOPIC OSSIFICATION;" and U.S. Provisional Patent Application No. 61/392,109 filed Oct. 12, 2010 and entitled "HYDROGEL MICROSPHERE ENCAPSULATION OF A CELL-BASED GENE THERAPY SYSTEM," the disclosures of which are incorporated by reference herein in their entirety.

STATEMENT REGARDING FEDERALLY SPONSORED RESEARCH OR DEVELOPMENT

This invention was made with government support under Defense Advanced Research Projects Agency (DARPA) W911NF-09-1-0040 and Department of Defense W81XWH-07-1-0215; W81XWH-07-1-0281. The U.S. Federal Government has certain rights in this invention.

TECHNICAL FIELD

The present invention generally relates to systems and methods for delivering bone morphogenetic proteins (BMP) to viable bone and other skeletal tissues. More particularly, the invention relates to delivery of BMP by encapsulated cell-based gene therapy systems. The delivery system may thus be applied to defective bone tissue and other viable tissue to induce formation of new bone.

BACKGROUND OF THE INVENTION

Although bone cells possess the capacity to repair major insults due to traumatic injury, degeneration or disease often requires surgical intervention and bone grafting. In the United States, approximately 550,000 million fractures annually require bone grafting. Further, of the over 1 million bone grafts performed annually worldwide, 50% involve spinal fusions and 25% of these patients complain of donor site pain from the autograft harvest site for up to two years post-operation. This number does not include the millions of total joint arthroplasties, spinal arthrodeses, maxillofacial surgeries and implant fixations that require bone replacement or repair. In an effort to circumvent the obstacles associated with grafts and complications involved in spinal fusions, researchers have used explored alternative methods such as the use of osteoinductive growth factors instead, including bone morphogenetic proteins ("BMPs"). In particular, BMPs possess the ability to induce heterotopic ossification or de novo bone formation at targeted locations. For example, the FDA recently approved BMP-2 for use in spinal arthrodesis.

Conventional delivery methods of BMP often include administration of isolated recombinant human BMP (rh-BMP) in relatively pure in solution to the targeted locations to induce bone growth. The patient's body, however, rapidly clears the BMP when the protein is administered in solution because BMPs are soluable. In particular, BMP cannot be localized and tends to diffuse from the desired site.

As such, the efficacy of BMP is reduced when it is administered by conventional methods, thereby requiring larger doses to attain a therapeutic effect. Because large quantities of the purified BMPs are required to compensate for the rapid diffusion and produce satisfactory bone healing, the grafting procedures can become very expensive. Further, the high dosage of BMP, e.g., supra-physiologic concentrations, may lead to adverse effects such as soft tissue edema, erythema, local inflammation, immune response, and bone resorption in the graft area. Consequently, despite the benefits provided by BMP, many clinicians have found rhBMP to have inconsistent efficacy, especially in complex clinical scenarios such as traumatic injury. These findings have led to a renewed emphasis to develop better methods of delivering BMP to and maintaining BMP at the targeted locations.

Other conventional methods addressed the rapid clearance problem by introducing a delivery system that can retain and sequester the BMPs at the implantation sites. The main role of the delivery system consequently is to retain the growth factor at the defect site for the bone regeneration and repair pertinent duration of time according to defect anatomical site, size and vascularity in order to allow the regenerative tissue forming cells to migrate to the defect area, proliferate and differentiate. For instance, purified BMPs have been integrated with gelatin foam or into collagen sponge or other implantable scaffolding carriers that show some degree of natural binding affinity to BMPs, such as collagen. In particular, the FDA has also approved rhBMP-2 for use on collagen sponges for the treatment of open long bone fractures and in metal cages for spinal fusion.

Unfortunately, these delivery systems have numerous disadvantages. For example, collagen can elicit an adverse immune response from the patient's body. Furthermore, collagen often presents handling difficulties because collagen paste only allows bone surrounding the paste to form but not elsewhere while free-form collagen would diffuse away from the targeted location. Also, the use of a collagen sponge or other implantable delivery devices would bind to the BMPs themselves, thereby reducing the bioavailability of BMPs. Thus, even larger amounts of purified BMP are necessary for a therapeutic response.

Moreover, with respect to spinal fusion, although the use of rhBMP for spinal fusion may negate the need for an additional surgical procedure to harvest autograft bone, current methods still necessitate an operation that introduces a permanent foreign object into the body. In particular, the use of BMP-2 to induce spinal fusion requires that the protein be implanted in a metal cage, leaving the treatment dependent on synthetic implants rather than being completely biological in nature. Further, autologous bone graft is often harvested to use in place of ectopic bone, which requires an additional extensive surgical procedure. Spinal fusion further requires (1) decortication of the transverse processes of the vertebrae targeted for fusion, (2) stripping of the paraspinous musculature from bone, and (3) a fairly long operative time. Beyond the pain associated with decortication and stripping are other complications. In particular, stripping the musculature compromises the stability afforded by these muscles, disrupts the blood supply to both bone and muscle, and promotes scar formation.

Gene therapy approaches hold much promise in achieving locally high levels of BMP for production of robust heterotopic ossification. However, the efficient transduction of cells posed a problem for many of the currently tested systems resulting in low BMP expression such as known methods of delivering adult stem cells (mesenchymal stem cells [MSCs] isolated from bone marrow, fat, and muscle, among others), along with osteoprogenitors and osteogenic factors to the site of interest. Further, this problem is then exacerbated by inclusion of a collagen sponge or other biomaterial that rapidly binds to the BMP, thereby further reducing its effectiveness. Moreover, although adenoviral vectors producing BMP2 (AdBMP2) have been used to elicit spinal fusion in rats, the transduced cells were surgically implanted with collagen sponges or demineralized bone matrix following decortication of lumbar transverse processes. Such inclusion of a biomaterial and invasive decortication procedures cause undesired inflammation, which potentially weakens bone healing. An example of such invasive procedures is described in Wang J C, Kanim L E A, Yoo S, et al. Effect of regional gene therapy with bone morphogenetic protein-2-producing bone marrow cells on spinal fusion in rats, *J of Bone and Joint Surgery* 2003; 85:905. Given these drawbacks, there is still a need for methods and systems that are biocompatible, biodegradable, osteoinductive and osteoconductive to effectively and economically deliver the desired amount of BMPs to the targeted locations at lower cost.

BRIEF SUMMARY OF THE INVENTION

One objective of the present invention is to provide methods for delivery of high levels of BMPs at targeted locations for rapid bone formation or heterotopic ossification.

Another objective is to provide methods to induce spinal fusion without invasive surgery or additional BMP carriers.

Yet another objective is to provide methods to repair critical size defects in bones.

Another objective of the present invention is to provide delivery systems for BMP that avoids rapid clearance of the BMP by the patient's body.

Another objective of the present invention is to provide systems that deliver BMP without the use of implantable carriers, such as sponges, thereby minimizing acute deleterious inflammatory reactions at the implantation sites.

Yet another objective of the present invention is to provide BMP carriers that allow for prolonged delivery of BMP locally at the target site while the carriers are degradable based on the properties of bone resorption and remodeling.

To meet the these objectives, there is provided methods and compositions for treating an individual (including a mammal, such as a human, dog, cat, horse, pig, goat, or sheep, for example) having a bone defect comprising the step of delivering, to a targeted bone defect of an individual, one or more BMP producing cells. In some embodiments, the one or more BMP producing cells are used to achieve spinal fusions and treat spinal arthrodesis. In spinal fusion applications, the present invention does not require additional hardware, or invasive surgery to decorticate the vertebral bone, but rather harnesses the body's capacity to rapidly produce heterotopic bone. In certain embodiments, the present invention targets the location of the heterotopic ossification, thereby forming new bridging bone between the vertebrae and obtaining fusion to adjacent skeletal bone without invasive surgery. The present invention also provides for reduction in spine flexion-extension.

In some embodiments, the delivery of BMP producing cells is by injecting the individual with microencapsulated adenovirus- or adenoassociated virus-transduced cells in poly (ethylene glycol) diacrylate (PEG-DA) hydrogels. In certain aspects, the microencapsulated BMP producing cells may be used to form bones of specific desired shapes and sizes at the targeted location. In other aspects, the microencapsulated BMP producing cells may be used to repair critical size bone defects. In yet other aspects, the microencapsulated BMP producing cells may be used to induce spinal fusion.

In other embodiments, at least one hydrogel microsphere is formed by forming a hydrogel precursor solution with PEG-DA, adding said hydrogel precursor solution to a volume of mineral oil, and emulsifying the mineral oil that has the hydrogel precursor solution already added. In certain embodiments, the hydrogel precursor solution is formed by combining 0.1 g/ml 10 kDa PEG-DA (10% w/v) with 1.5% (v/v) triethanolamine/HEPES buffered saline (HBS, pH 7.4), 37 mM 1-vinyl-2-pyrrolidinone, 0.1 mM eosin Y, and transuduced cells. In other embodiments, acetephenone was added to mineral oil and mixed well. The microspheres were formed after adding the hydrogel precursor solution into the mineral oil and emulsifying by vortex. In one embodiment, the PEG-DA is non-degradable, while in other embodiments, the PEG-DA is degradable by enzymes produced during bone formation. In particular embodiments, PEG hydrogels with a cathepsin K sensitive peptide sequence GPSG incorporated into the polymer backbone are used as degradable carriers where they can be gradually degraded with cathepsin K secreted by osteoclasts during bone resorption processes.

In certain embodiments, the hydrogel microspheres containing the transduced cells are collected and delivered to the bone defect via a syringe. In other embodiments, the microspheres contains 0-100 transduced cells configured to produce bone morphogenetic protein. In some embodiments, the average radius of the microspheres is in the 50-150 μm range. In another embodiment, the cells used for transduction are fibroblasts and/or mesenchymal stem cells, or other primary cells that can be readily expanded and transduced ex vivo. In yet another embodiment, the virus is replication defective. In certain embodiments, the microspheres include both the transduced cells and one or more vascular agents.

The foregoing has outlined broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and specific embodiment disclosed may be readily used as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 4G shows the appearance of the mature cortical bone of the vertebra during its apparent removal and replacement by the maturing heterotopic bone.

FIGS. 10E and 10F show a pattern of dense bone surrounding a hollow interior.

It should be understood, of course, that the invention is not limited to the particular embodiments illustrated herein. In certain instances, details that are not necessary for an understanding of the disclosed methods and apparatuses or that render other details difficult to perceive may have been omitted.

DETAILED DESCRIPTION

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein. The above term descriptions are provided solely to aid the reader, and should not be construed to have a scope less than that understood by a person of ordinary skill in the art or as limiting the scope of the appended claims.

Figure 1:
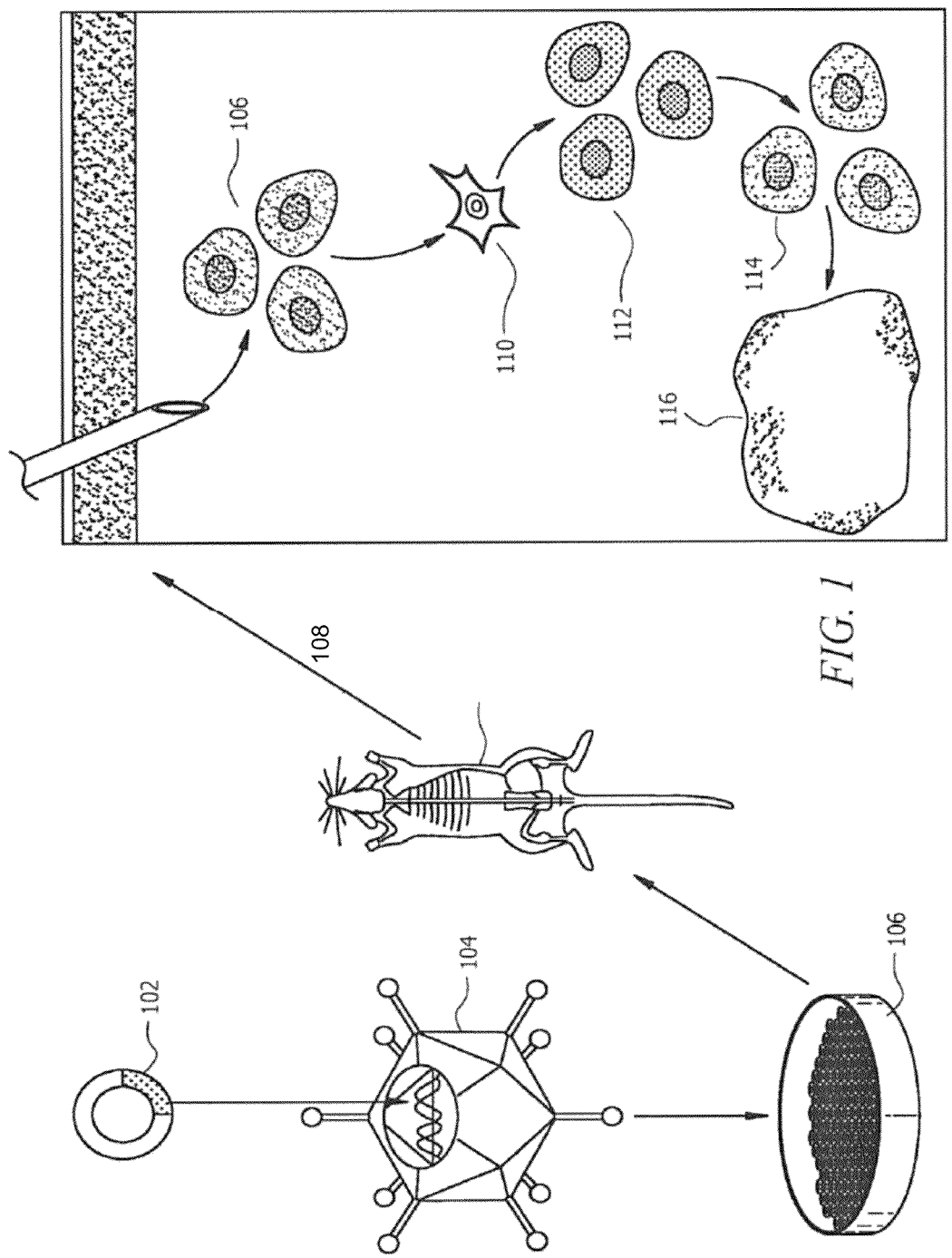
FIG. 1 is a schematic depiction of the cell based gene therapy system according to one aspect of the present invention.

The delivery system of this invention induces formation of bone by the host without the difficulties involved in other gene- and stem cell-based systems discussed above including isolating stem cell populations (e.g., MSCs) to use as delivery cells and low gene transduction efficiencies. Examples of these cell- and gene-based systems are disclosed in Kimelman et al., *Tissue Eng* 13, 1135 (June, 2007). Referring to FIG. 1, in one embodiment, the desired BMP gene 102 is packaged into an adenoviral vector 104. While the preferred embodiment uses BMP-2, other embodiments may use other BMP genes known to those skilled in the art, e.g., BMP-1, BMP-3, BMP-4, BMP-5, BMP-6, BMP-7, BMP-8a, BMP-8b, BMP-10, BMP-11, BMP-12, BMP-13, BMP-14, and BMP-15, or genes for similar cytokines that also induce bone growth. In the preferred embodiment, replication defective E1-E3 deleted first generation human type 5 adenovirus (Ad5) or a human type 5/35 adenovirus (Ad5F35) in which the normal fiber protein has been substituted for the human adenovirus type 35 fiber (Ad5F35) are used based on their efficiency for transducing either human or mouse cells. Other embodiments, however, may employ other viruses, such as adeno-associated virus, that do not integrate into the chromosome of the transduced cells, and thus, are similarly effective for transducing either human or other mammal cells.

Referring to FIG. 1, the adenovirus 104 is incubated ex vivo with cells 106 to transduce the BMP gene 102 into cells 106. In some embodiments, cells 106 comprise human diploid fetal lung fibroblasts (MRC-5) and murine osteoblasts (MC3T3-E1). Other embodiments may use different cells such as allogeneic or autologous skin fibroblasts, mesenchymal stem cells or other primary cells that can be readily expanded and transduced ex vivo, whether from human or other mammals. The examples discussed below provide additional details of the incubation conditions for transduction. However, these examples are not intended to limit the scope of the present invention as other transduction procedures known to those skilled in the art can also be used.

Subsequently, the genetically modified cells 106 are injected into the subject 108, which can be any mammal such as a human, dog, cat, horse, pig, goat, or sheep, for example. Preferably, the tranduced cells 106 are injected intramuscularly. However, in other embodiments, the cells 106 may be injected at other desired bone defect locations known to those skilled in the art. The cells may be injected by resuspension in saline and endoscope-guided or non-guided percutaneous injection into the target site for the desired bone formation. In the body of subject 108, the transduced cells 106 produce and release proteins 110 encoded by the transduced BMP gene 102. The proteins 110 in recruit host cells to undergo all stages of endochondral ossification, such as the chemotaxis and proliferation of mesenchymal stem cells, which can differentiate into chondrocytes 112 and/or osteoblasts 114, forming new bone 116.

During adenovirus transduction, multiple virus particles enter the cells 106 with large amounts of vector DNA effectively delivered to the nucleus of cells 106. Because of its episomal nature, the vector DNA is present at high copy number, driving high-level expression of BMP. Therefore, one of the things separating adenovirus from other gene therapy vectors is the high level of transgene expression that can be achieved after efficient transduction. As long as the virus can efficiently infect the specific cell types, the system of the present invention can be used to produce these high doses of BMP. Thus, the present invention provides a cell based gene therapy system rather than a direct approach to circumvent (1) potential problems with inefficient uptake of the adenovirus by stem cells and (2) problems that prohibit production of the BMP levels necessary to induce bone growth.

Further, the transduction of the cells 106 with the virus 104 prior to injection into subject 108 of the present invention ensures that no free adenovirus is delivered to the animal. As such, the adverse effects of the virus on other tissues is minimal as compared to other known delivery systems. Consequently, the present invention provides an efficient BMP delivery system that is independent of cell line, permitting the transduction of any type of cell and continual delivery of functional BMP to the target site over a prolonged period. Furthermore, the present invention provides for high transduction efficiencies, requiring only a modest quantity of cells for a therapeutic effect as compared to other known methods of delivering BMPs to the desired location. Particular applications of the present invention include delivering sufficient BMPs to the desired locations to form bone of specific shape and size, specifically spinal fusions and treatment of critical bone defects. For instance, the transduced cells 106 may be injected into or near the paraspinous muscles along the length of the spine to induce spinal fusion. Prior studies that may employ AdBMP2 to elicit spinal fusion fails to take into account the fact that without manipulation of the cells prior to transduction, the adenoviral vectors can only minimally elicit bone formation if at all. Unlike these prior spinal studies, the present invention treats the cells with lipid polyamine as part of the transduction procedure, thereby providing high transduction efficiencies by allowing attachment and internalization of the adenovirus in the cells.

Figure 2:
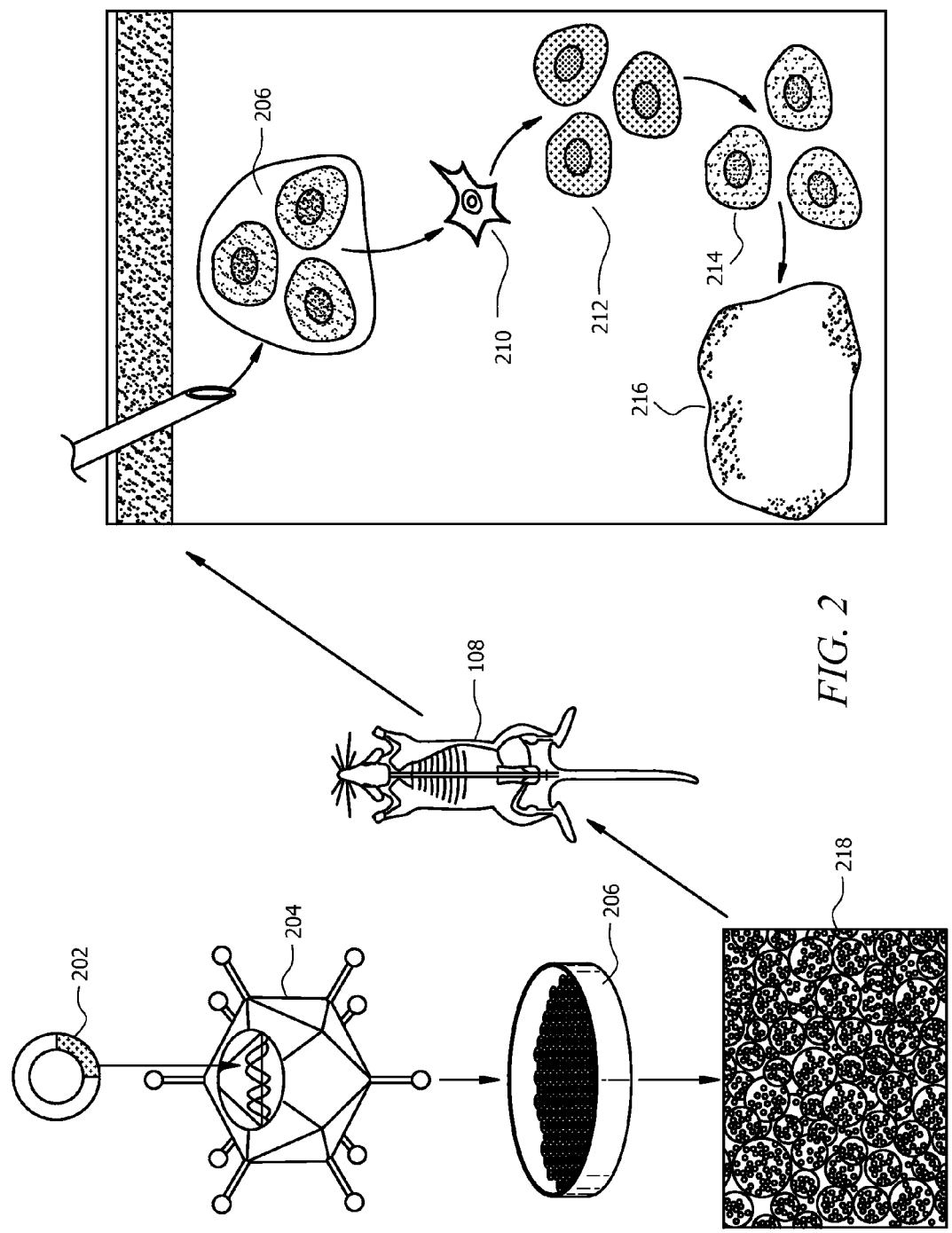
FIG. 2 is a schematic depiction of the encapsulated cell based gene therapy system according to one aspect of the present invention.
Figure 3:
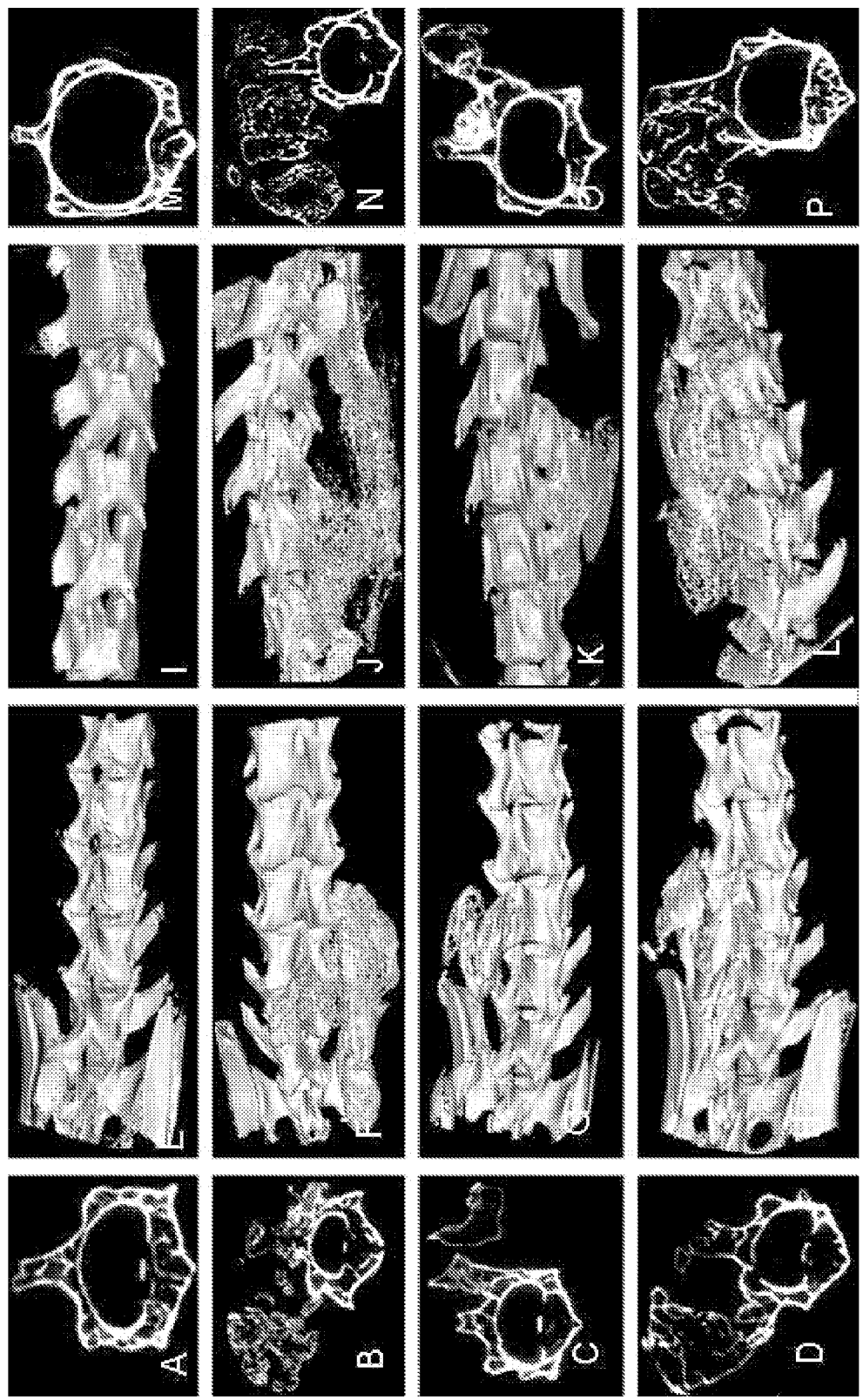
FIG. 3 presents radiographs of C57BL/6 (panels A-H) and NOD/Scid (panels I-P) spines imaged after intramuscular injection into the paraspinous musculature of cells transduced with Adempty cassette control virus (panels A, E, I, and M) or AdBMP2 (panels B-D, F-H, J-L, and N-P). Control animals injected with Ad5HM4 were scanned 6 weeks after delivery of the transduced cells (panels A, E, I and M). Mice receiving the AdBMP2 transduced cells, were scanned 2 weeks (panels B, F, J, N); 4 weeks (panels C, G, K, 0); and 6 weeks (D, H, L, P) after the initial induction of heterotopic ossification. Two dimensional x-rays (panels A-D; C57BL/6 and panels M-P; NOD/Scid) show a cross section through the three dimensional reconstructions (panels E-H; C57BL/6 and I-L; NOD/Scid) of tentative fusions between the heterotopic ossification and the vertebral bone.

In other embodiments, the capability of the transduced cells of the present invention to locally deliver BMP for a prolonged period may be further enhanced by encapsulating the transduced cells. Referring to FIG. 2, the transduced cells 206 of the present invention are generated in the same manner as cells 106 described above. That is, the desired BMP gene 202 is packaged into an adenoviral vector 204, which is incubated ex vivo with cells 206 to transduce the BMP gene 202 into cells 206. In certain embodiments, cells 206 are encapsulated into microspheres 218 before they are injected into subject 208 to further prolong the expression of the BMP within the injected tissues. In the preferred embodiment, poly (ethylene glycol) diacrylate (PEG-DA) hydrogels are used to encapsulate cells 206 that produce and secrete high levels of BMP. Hydrogels are insoluble networks of polymer chains that swell in aqueous solutions. PEG-DA hydrogels are bio-inert and mimic many physical properties of the extracellular matrix of soft tissue. Physical characteristics of hydrogels such as stiffness and permeability can be designed to better approximate a tissue of interest, to regulate nutrient/waste diffusion, or to prevent interaction with immune cells. While it is known that hydrogels may provide immunoprotection, other previous attempts to encapsulate certain transduced cells have resulted in a significant decrease in protein expression as compared to the expression of un-encapsulated cells. One such failed attempt is disclosed in Bikram, M. et al. Endochondral Bone Formation from Hydrogel Carriers Loaded with BMP2-transduced Cells. *Annals of Biomedical Engineering* 35, 796-807 (2007). Specifically Bikram encapsulates certain transduced cells into larger structures, e.g., large ratio between the number of cells and hydrogel, which caused substantial cell death. The present invention, on the other hand, provides certain encapsulation aspects that further enhance the BMP expression of the transduced cells 206 to retain an even higher level of BMP expression from transduced cells 206.

Further, encapsulating the cells 206 according to the present invention spatially controls the gene expression and restricts immune clearance of the delivery of the cells 206. Unlike previous failed attempts to encapsulate other transduced cells into a single large structure, e.g., a large number of cells per bead, the present encapsulates the transduced cells 206 into microspheres. In the preferred embodiment, each microsphere holds about 0-100 transduced cells. The examples discussed below provide additional details of the microencapsulation process. However, these examples are not intended to limit the scope of the present invention as other similar materials known to those skilled in the art can also be used. Particular applications of the encapsulated transduced cells of the present invention include delivery of sufficient BMPs to the desired locations to form bone of specific shape and size, such as inducing spinal fusions, treatment of critical bone defects or any other bone defects that require new bone formation, or extending the length of a limb. In some embodiments, vascular agents such as vascular endothelial growth factor (VEGF) may be included during the formation of the microspheres such that both the transduced cells and vascular agents may be encapsulated together and are secreted from the microspheres in the subject's body, either together and or separately.

Moreover, the present invention demonstrates the ability of heterotopic ossification to form bridging bone and fuse adjacent vertebral bone without contribution from the skeletal bones. Further, the present invention provides targeted heterotopic bone formation to a discrete location. After initial injection of the AdBMP2 transduced cells, heterotopic bone was found between the transverse process adjacent to the paraspinous musculature receiving the cells and laminae. This heterotopic bone eventually encompassed these structures, fusing the spine. Histological analysis of this model demonstrate that the heterotopic bone grows into the skeletal bone with an organized growth plate, cortex, and tentative periosteum, similar to the vertebral bone. This process allows for the replacement of the cortical boundary with mature trabecular bone and bone marrow over time. The developed structures are well fused both histologically and biomechanically.

In another aspect of the present invention, microencapsulation further enhances the capability of the transduced cells of the present invention to induce bone formation. As such, microencapsulation provides local delivery of BMP via injection that avoids any required surgery to harvest the cells of the patient and prevents rapid clearance of the BMP or the cells from the injection site, and thereby extending the delivery of BMP to induce bone formation. Further, the microencapsulation of the present invention minimizes immune response to the polymer and does not bind BMP2. As such, unlike other carriers, the present invention does not limit any bioavailability of the produced BMP. Because the present invention provides for high transduction efficiencies, only a modest quantity of cells and microspheres is required for a therapeutic effect.

Furthermore, the microencapsulation aspect of the invention provides for a more exact spatial placement of the transduced cells and produce bone of in a desired location and size. As such, the present invention can be implemented in the therapy to traumatic bone injury. Moreover, spreading out the region in which BMP-2 is expressed through microsphere delivery provides a significant increase in the volume of bone and decrease in bone density. Despite the hydrogel's capacity to dictate the shape of the newly forming bone, it does not interfere with the structural patterning that is part of the biology of bone formation.

Accordingly, the embodiments of the present invention are versatile and independent of cell line, permitting the transduction of any type of cell, and, with efficient transduction, delivering functional BMP continually to the target site over a prolonged period. Thus qualified cell lines used in current clinical trials, such as mesenchymal stem cells, can be readily adapted for use in this cell based gene therapy system, making it very feasible to introduce clinically. The present invention provides for the fusing of the spine without surgical intervention. In particular, the present invention achieves spinal fusion with the creation of a bony fusion by means of the percutaneous injection of a biologically active material, without extensive surgical dissection and bony decortications that are required in traditional spinal fusion processes.

EXAMPLE 1

Spinal Fusion by Injection

Cell Culture

Human diploid fetal lung fibroblasts (MRC-5) and murine osteoblasts (MC3T3-E1) were obtained from the American Type Culture Collection (ATCC; Manassas, Va.) and propagated in a humidified incubator at 37° C. and 5% $CO_2$ in α-minimum essential medium (α-MEM; Sigma, St. Louis, Mo.) and Dulbecco's Modified Eagle's Medium (DMEM; Sigma, St. Louis, Mo.) supplemented with 10% fetal bovine serum (FBS; HyClone, Logan, Utah), 1000 U/L penicillin, 100 mg/L streptomycin, and 0.25 µg/ml amphotericin B (Invitrogen Life Technologies, Gaithersburg, Md.), as described in Fouletier-Dilling, C. et al. Efficient and Rapid Osteoinduction in an Immune-Competent Host. *Human Gene Therapy* 18, 733-745 (2007) and C. M. Fouletier-Dilling et al., *Hum Gene Ther* 16, 1287 (November, 2005). Murine stromal cells (W20-17; a gift from Genetics Institute, Cambridge, Mass.) were propagated and maintained as described by Thies, R. Recombinant human bone morphogenetic protein-2 induces osteoblastic differentiation in W-20-17 stromal cells. *Endocrinology* 130, 1318-1324 (1992).

Adenoviruses

Replication defective E1-E3 deleted first generation human type 5 adenovirus (Ad5) or a human type 5/35 adenovirus (Ad5F35) in which the normal fiber protein has been substituted for the human adenovirus type 35 fiber (Ad5F35) were constructed to contain cDNAs for human BMP2 in the E1 region of the viruses as described in A. R. Davis, N. A. Wivel, J. L. Palladino, L. Tao, J. M. Wilson, *Mol Biotech* 18, 63 (May, 2001). Two independent viruses were used based on their efficiency for transducing either human or mouse cells as described by N. Kimelman et al., Tissue Eng 13, 1135 (June, 2007). For the viruses Ad5BMP2, Ad5F35BMP2, Ad5-empty cassette, and Ad5F35empty cassette, the viral particle (VP)-to-plaque-forming unit (PFU) ratios were 55, 76, 200, and 111, respectively, and all viruses were confirmed to be negative for replication-competent adenovirus. Ad5 viruses were used for the murine MC3T3-E1 cells and Ad5F35 viruses were used for the human MRC-5 cells. Additional information on the construction, propagation and purification of the adenoviral vectors used in this study is also disclosed in Fouletier-Dilling C, Bosch P, Davis A, et al. Novel compound enables high-level adenovirus transduction in the absence of an adenovirus-specific receptor. Human Gene Therapy 2005; 16:1287-97 and Davis A, Wivel N, Palladino J, et al. Construction of adenoviral vectors. Molecular Biotechnology 2001; 18:63-70.

Cell Transduction

Cells from the murine cell line MC3T3-E1 ($1 \times 10^6$) were transduced with a BMP2 adenoviral vector or control (AdBMP2 or AdEmpty, respectively) at a viral concentration of 5000 VP/cell with 1.2% GeneJammer®, as described in Fouletier-Dilling C, Bosch P, Davis A, et al. Novel compound enables high-level adenovirus transduction in the absence of an adenovirus-specific receptor. Human Gene Therapy 2005; 16:1287-97. Generally, GeneJammer® was added at 3% to α-MEM without supplements to and incubated for 10 minutes at room temperature. Ad5BMP2 or Ad5-empty was then added at the aforementioned concentrations and the mixture was further incubated for 10 minutes at room temperature. This virus solution was then diluted with supplemented α-MEM to achieve 1.2% GeneJammer® per volume. The resulting solution was next incubated at 37° C. for 4 hours with cells at an amount that is sufficient to just coat the cells, and then the mixture was diluted with supplemented medium at an amount appropriate for cell culture and incubated at 37° C. overnight. MRC-5 human fibroblasts ($1 \times 10^6$) were transduced with a BMP2 adenoviral vector or control, AdBMP2 or AdEmpty, respectively, as described in Davis A, Wivel N, Palladino J, et al. Construction of adenoviral vectors. Molecular Biotechnology 2001; 18:63-70. Generally virus was added at a viral concentration of 2500 VP/cell to fresh supplemented DMEM and incubated with cells in a humidified incubator with 5% $CO_2$ at 37° C. overnight.

BMP-2 Quantification

BMP-2 expression was evaluated for MC3T3 and MRC-5 cells transduced with Ad5BMP2, Ad5-empty, Ad5F35BMP2 or Ad5F35HM4 using ELISA and alkaline phosphatase assays. Culture supernatant from transduced cells were collected 72 hours after adenovirus transduction and assayed with a BMP-2 Quantikine ELISA kit from R&D Systems (Minneapolis, Minn.) to measure BMP-2 expression. Transduced cells were cultured in 0.4 µm pore polycarbonate membrane transwell inserts (Corning Inc., Lowell, Mass.), and W20-17 cells were cultured in the wells of 6 well plates. After 72 hours, W20-17 cells were assayed for alkaline phosphatase activity using a chemiluminescence procedure. Three freeze-thaw cycles were performed in a 100-µM/cm² concentration of 25 mM Tris-HCl (pH 8.0) and 0.5% Triton X-100 in order to extract cellular alkaline phosphatase and this activity was then measured by adding a ready-to-use CSPD substrate with Sapphire-II enhancer (Tropix; Applied Biosystems, Foster City, Calif.) to the samples. After a 2-second delay, the light output from each sample was integrated for 10 seconds with a luminometer (TD-20/20; Turner BioSystems, Sunnyvale, Calif.). Alkaline phosphatase levels were recorded in relative luminescence units (RLU) and normalized to protein content with the bicinchoninic acid (BCA) assay, using bovine serum albumin to derive a standard curve. BMP2 protein levels and functional activity were found to be similar to previously published results per cell number and virus dose, e.g., E. A. Olmsted-Davis et al., Hum Gene Ther 13, 1337 (Jul. 20, 2002).

Injection of the Transduced Cells for Spinal Fusion

Female non-obese diabetic severe compromised immune deficiency (NOD/SCID; n=44) and C57BL/6 (n=43) mice (8-12 weeks old; Charles River Laboratories; Wilmington, Mass.) were maintained in accordance to Baylor College of Medicine Institutional Animal Care and Use Committee (IACUC) protocols. Each mouse strain was separated into two major groups: (1) animals receiving control transduced cells or (2) animals receiving BMP2 transduced cells. In particular, NOD/SCID animals received AdBMP2 (n=35) or AdEmpty (n=9) transduced cells while C57BL/6 mice received AdBMP2 (n=32) or AdEmpty transduced (n=11) cells. Animals receiving AdBMP2 transduced cells were further divided into groups to be harvested at 2, 4 and 6 weeks (for C57BL/6, n=8, 4 and 20, respectively; for NOD/SCID, n=11, 12 and 12, respectively). All animals receiving AdEmpty transduced cells were harvested at 6 weeks.

Prior to paraspinous injections, the back of each mouse was prepared and a limited portion of the skin was incised to reveal the paraspinous muscles. Although the injection could have been conducted without opening the skin, the incision was performed to ensure appropriate placement of the transduced cells. Transduced cells were collected for injection after removal from tissue culture plates with trypsin and resuspension in phosphate buffered serum (PBS) at a concentration of $5 \times 10^6$ cells per 100 µl of PBS, and then delivered by intramuscular injection into the right paraspinous muscles along the length of the spine. The placement of the needle was performed manually. The needle was positioned within the longissimus muscle, 1 to 2 mm distant from the lamina and spinous process. Multiple deliveries of approximately 10 µl of cell suspension were injected at about 2 or 3 mm intervals along the spinal segment targeted by advancing the needle without completely withdrawing it. Cells were not injected with the needle in contact with the bone. A total of volume of 50 µl was injected for each animal. After 2, 4 and 6 weeks, mice were sacrificed and the spines with attendant musculature were removed and fixed at room temperature overnight in 4% formaldehyde solution (VWR; Sugar Land; TX).

Microcomputed Tomography (MicroCT) Analysis

All harvested intact spines (N=87) were scanned at 14 µm resolution with a commercial microCT system (GE Locus SP, GE Healthcare, London, Ontario). Three dimensional reconstructions of the spine and any mineralized tissue in the surrounding muscle were created at 29 µm resolution to visualize endochondral mineralized tissues. A volume of interest was defined for each specimen, and a threshold was chosen to exclude any non-mineralized tissue. The total volume of endochondral bone was then measured (eXplore MicroView, v. 2.0, GE Healthcare, London, Ontario) and preexisting bone from the spines of the animals were excluded from mineralized tissue measurements.

Biomechanical Testing

Figure 5:
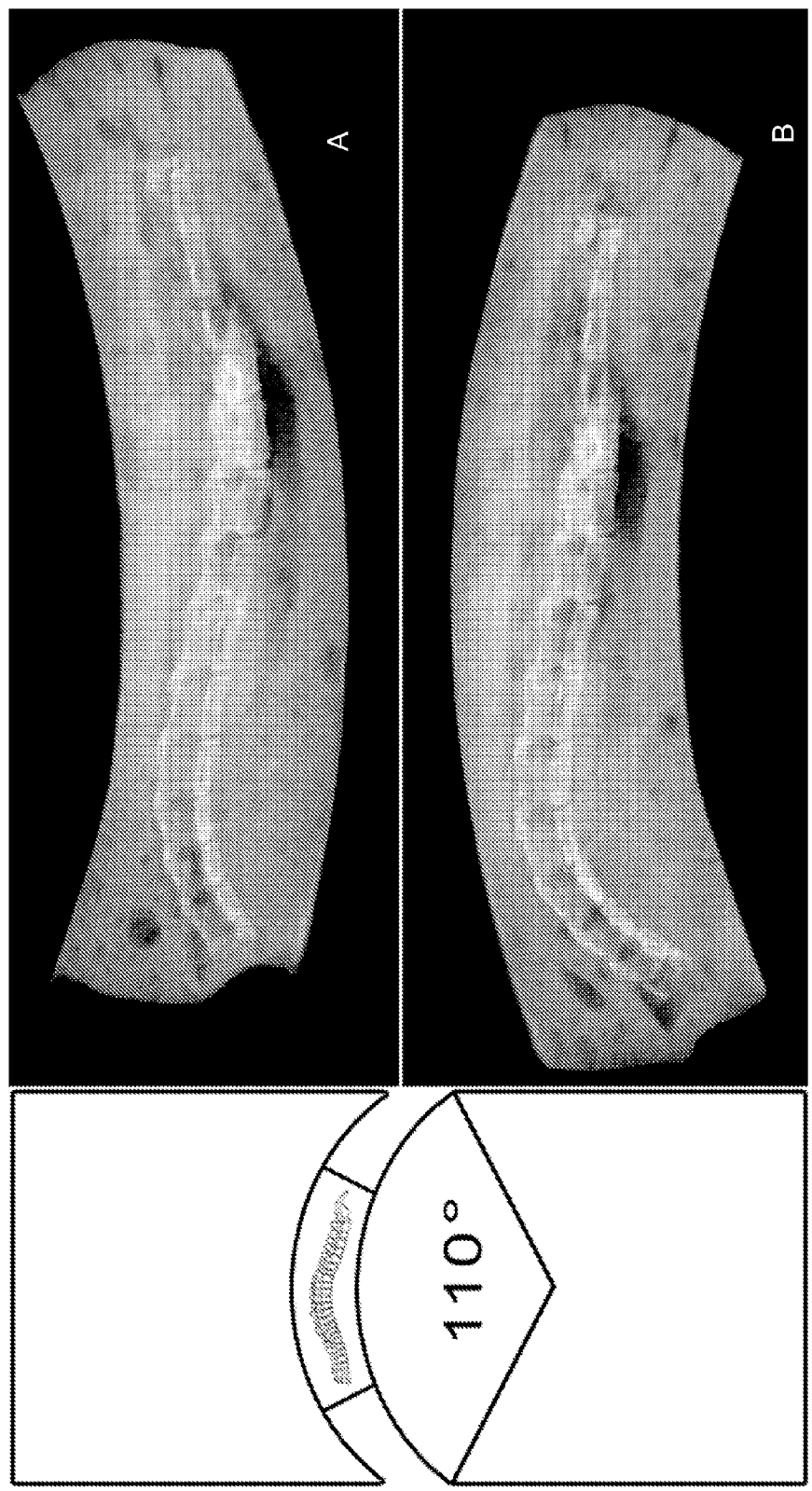
FIG. 5 shows representative images used to evaluate biomechanical function of spinal fusion. After 2, 4 or 6 weeks, spines were harvested, placed in the device to induce flexion or extension at 110° and radiographed. Panel A shows the spine in extension, and panel B shows the spine in flexion. The images were evaluated with KIMAX QMA software (Medical Metrics, Inc.) to determine whether adjacent vertebrae moved past a predetermined threshold.

After microCT, formaldehyde fixed spines from each group (n=64) were encased in alginate in order to obtain flexion and extension radiographs. Spines with attendant soft tissue from the C57BL/6 mice, AdEmpty (n=8; 6 wk), AdBMP2 (2 wk, n=8; 4 wk; n=4; 6 wk, n=8) and from the NOD/SCID mice (n=9, each group) were suspended in an in-house mold. Alginate powder was combined in an equal volume to water (30 ml of each) and mixed until smooth. The alginate was poured into the mold and allowed to solidify such that no portion of the spine protruded from the solidified alginate. Solidified alginate blocks were placed in an in-house spring loaded clamp with rigid 110° arcs (FIG. 5). Radiographs were taken of molds in flexion and extension orientations for each spine. These digitized radiographs were used to quantify intervertebral motion with Food and Drug Administration (FDA) approved software (KIMAX QMA, Medical Metrics, Inc.) that has been validated for the clinical assessment of spinal fusion by measuring relative intervertebral motion. The software compares radiographs in extension and flexion, detects the concomitant intervertebral rotation and translation and has been demonstrated to report movement with an accuracy better than 0.5° for rotation and 0.5 mm for translation between adjacent vertebrae. Intervertebral motion was measured at each vertebral level. Preliminary data (not shown) demonstrated that the normal mouse spine undergoes an average of 5° of intervertebral motion using this test. Spines were considered fused when adjacent vertebrae did not exhibit rotation beyond 1.5°, which represents a 70% reduction in motion.

Histological Analysis

After biomechanical testing, four fixed spines from each group and time point (n=32) were isolated for histological analysis as previously described to confirm that any apparent mineralized bone observed on the radiographs was true osteoid and that it had integrated at these tentative points of fusion. The spines and adjacent tissues were decalcified in hydrochloric acid, processed and embedded into a single paraffin block, where serial sections were then cut at a thickness of 5 µm. Every fifth section was stained with hematoxylin and eosin and observed under light microscopy to identify the tentative points of fusion. Representative photomicrographs (2× and 4×) of samples from each model were taken 2, 4 and 6 weeks after induction of heterotopic ossification. To further confirm the vertebral fusion, a subset of spines (n=9; one from each group and time point, two from NOD/SCID at 6 weeks) were immersed in bleach for approximately one hour, which removed all soft tissues. Midway through this process, nylon wire was threaded up the spinal canal in order to maintain the relative position of the vertebrae.

Statistical Analysis

Statistical analysis was performed as described in C. M. Fouletier-Dilling et al., *Hum Gene Ther* 18, 733 (August, 2007) and C. M. Fouletier-Dilling et al., *Hum Gene Ther* 16, 1287 (November, 2005). Generally, all data were taken in triplicate and reported as mean and standard deviation. A Student t test with 95% confidence interval (p<0.05) was done between the untreated control and each experimental condition.

Radiological Analysis of Bone Formation

In all animals receiving AdBMP2 transduced cells, heterotopic bone formation occurred along the injection site adjacent to the spine, with greater than 90% of all animal spines showing bridging and fusing to the skeletal bone (FIGS. 3F-3L) by 4 weeks (NOD/SCID 89% and C57BL/6 mice 100%). Two dimensional microCT images show cross sections through the injected area (FIGS. 3A-D, 3M-P). The radiographs and three dimensional reconstructions demonstrate that both the immune incompetent system, NOD/SCID mice receiving human cells transduced with AdBMP2 (FIG. 3I-P), and immune competent system, C57BL/6 mice receiving AdBMP2 transduced allogeneic murine cells (FIG. 3A-H), produce similar bone within 4 to 6 weeks. In particular, the newly formed heterotopic bone appears to have integrated into the vertebral cortical bone (FIG. 3B-D, 3O-P). These points of fusion appear to be in the laminae region of the vertebra, with most of the fusions encompassing the entire spinous and transverse processes, demonstrating robust significant fusion. This new bone appears to be remodeled with a contiguous cortical bone exterior. The inventors did not observe any bone formation or bridging in the mice receiving the Adempty cassette transduced cells. The spinal fusion occurred rapidly in the mice receiving the cells transduced with BMP, e.g., within two weeks. The spinal fusion also occurred in size and scale that corresponds to the region of muscle that received the cells transduced with BMP.

Biomechanical Analysis to Confirm Reduced Motion of the Spine

The inventors confirmed that the spinal fusion achieved according to certain aspects of the present invention also reduces motion within the vertebral column by measuring flexion-extension of the spine of the treated mice. Comparisons of harvested spine radiographs subjected to 110° of flexion and extension revealed reduced intervertebral motion in animals receiving AdBMP2 (FIG. 5). Spines were considered fused when the KIMAX QMA software (Medical Metrics, Inc.), which is used to report clinical fusions indicated that relative intervertebral rotation between adjacent vertebrae was reduced by 70% of normal. Results of this analysis are shown in Table 1. When analyzed for relative intervertebral rotation and translation, in no cases did tissues receiving AdEmpty transduced cells show a reduction in motion or spine stiffening. Conversely, in NOD/SCID animals that received the human cells transduced with AdBMP2, approximately 44% of the spines at 2 weeks and 89% of those at 4 and 6 weeks had reduced movement, consistent with fusion of at least one level. In the C57BL/6 group receiving murine AdBMP2 transduced cells, 100% of the spines at all time points consistently showed a reduction in motion correlating with fusion. The biomechanical testing measured the changes in angle of the spine under force. The inventors observed that the fused spines achieved according to certain aspects of the present invention have well integrated collagen fibers running contiguously through the bone, demonstrating that they were a remodeled single structure.

TABLE 1

Spinal fusion in injected animals

| Group | N | Strain | Time | Spines with 2 or more vertebrae fused (%) |
|---|---|---|---|---|
| Adempty cassette transduced cells | 9 | NOD/Scid | 6 weeks | 0% |
| AdBMP2 transduced cells | 9 | NOD/Scid | 2 weeks | 44% |
| AdBMP2 transduced cells | 9 | NOD/Scid | 4 weeks | 90% |
| AdBMP2 transduced cells | 9 | NOD/Scid | 6 weeks | 90% |
| Adempty cassette transduced cells | 8 | C57BU6 | 6 weeks | 0% |
| AdBMP2 transduced cells | 8 | C57BU6 | 2 weeks | 100% |
| AdBMP2 transduced cells | 4 | C57BU6 | 4 weeks | 100% |
| AdBMP2 transduced cells | 8 | C57BU6 | 6 weeks | 100% |

Histological Analysis of the Spine Fusion

Figure 4:
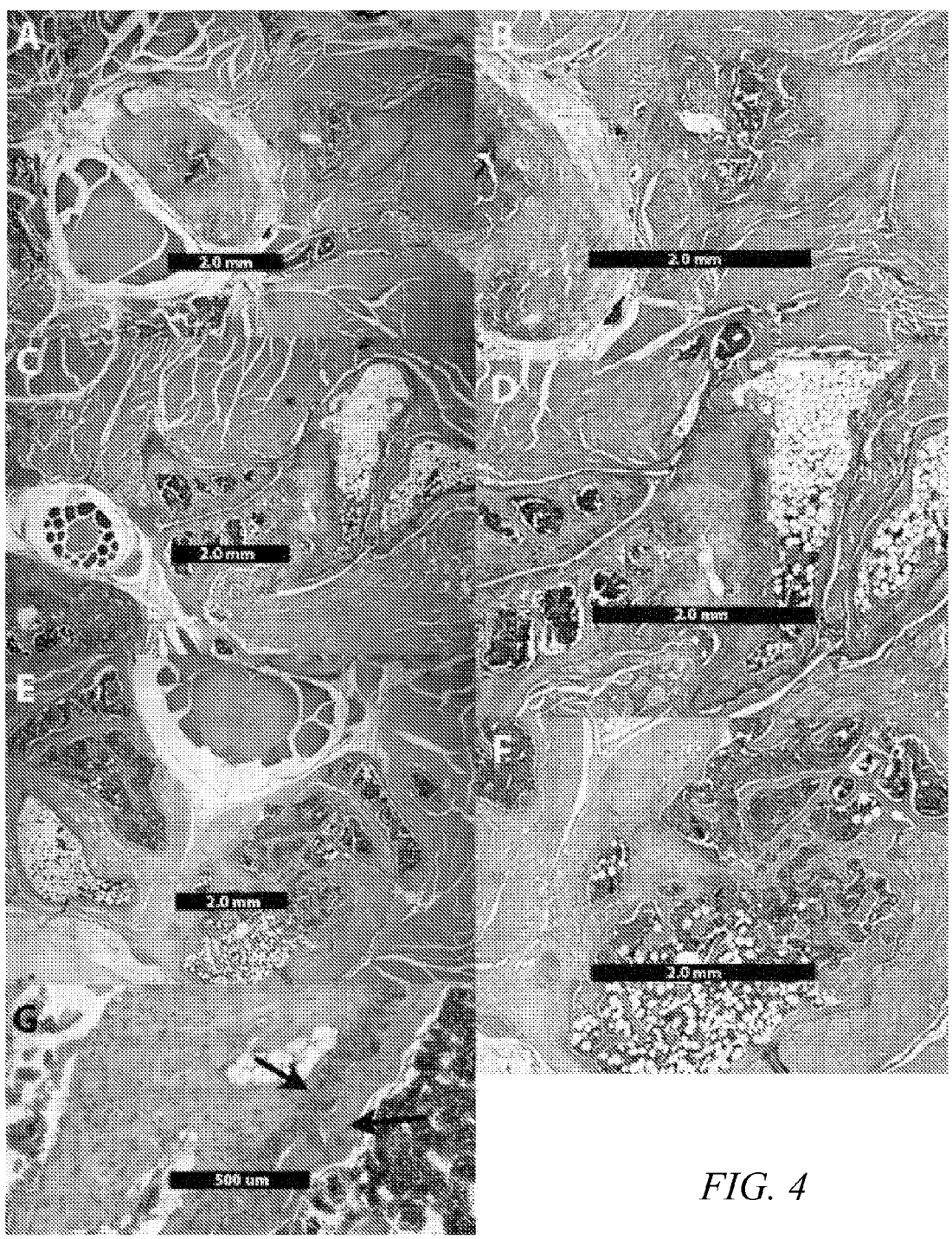
FIG. 4 presents representative photomicrographs of tentative vertebral fusion with the heterotopic bone, taken 2 weeks (panels A-B; 2× and 4× respectively), 4 weeks (panels C-D; 2× and 4× respectively), and 6 weeks (panels E-F; 2× and 4× respectively) after initial injection of the AdBMP2 transduced cells. The slides were stained with hematoxylin and eosin for viewing. Panel E is a representative photomicrograph (10×) of a sample taken 4 weeks after the initial injection of AdBMP2 transduced cells. As can be seen in this sample, there are a significant number of cells associated with the boundary between the new heterotopic and old vertebral bone.

The inventors confirmed that the newly formed mineralized bone is true osteoid and that it has integrated at these tentative points of fusion. The confirmation was done by isolating the spine and adjacent tissues for histological analysis using techniques described in E. Olmsted-Davis et al., *Am J Patho* 170, 620 (February, 2007). In particular, hematoxylin and eosin stained slides revealed structures of mature bone in all de novo bone samples from animals receiving BMP2 transduced cells (FIG. 5). Osteoclasts, osteocytes and tentative bone marrow elements in the heterotopic bone were observed in these slides, as well as cartilage, analogous to the growth plate structures in the normal long bone. The new heterotopic bone appeared to grow in a direction towards the skeletal bone, with the most mature bone being distant from the skeletal bone in the 2 week samples. There is substantial new bone adjacent to and fused with the more mature vertebral bone along the transverse process and laminae region of the vertebra (FIG. 4A-B). Although mature bone with tentative marrow elements was observed at 2 weeks, this structure was always distal to the vertebral bone (data not shown), suggesting that the original heterotopic ossification started de novo in the muscle and grew towards the vertebrae to encompass the existing bone.

At the four week time point (FIG. 4C-D) the heterotopic bone displays a much more mature morphology and a cellular process appears to be rapidly removing the mature cortex of the skeletal bone at the point of fusion. This large number of cells involved in this process has resulted in a moth-eaten appearance of the mature cortical bone of the vertebra during its apparent removal and replacement by the maturing heterotopic bone (FIG. 4G). The origin of the large number of cells is unclear. At the 6 week time point, the cortical boundary is completely remodeled (FIG. 4E-F) with the newly formed and original bone contiguous as one integrated structure with a well defined cortex and trabecular interior, which houses the bone marrow. At this point, the only evidence distinguishing the newly formed heterotopic ossification is the presence of substantial amounts of adipose tissue, which is found within heterotopic regions in contrast to the mature marrow within the vertebra (FIG. 4F).

All cases (FIG. 4) show what appears to be fusion with the transverse process within the laminae region of the vertebra, which was the target region for fusion. Depending on the depth of the histology section, more or less of this region was involved in the fusion site. In many cases the fusion actually encompassed both the spinous process through the laminae to the transverse process. In all tissues analyzed, the HO appeared to grow into the vertebral body, which itself did not appear to undergo growth, and there was no evidence of new bone formation within the spinal canal, similar to radiological findings. This demonstrates that the spinal fusion generated by the present invention did not induce additional adverse bone growth such as spurs, or heterotopic ossification within the spinal canal, which could potentially be damaging to the spinal nerves and could result in significant pain. In particular, it shows that the bone fusion of the present invention is not invasive.

Figure 6:
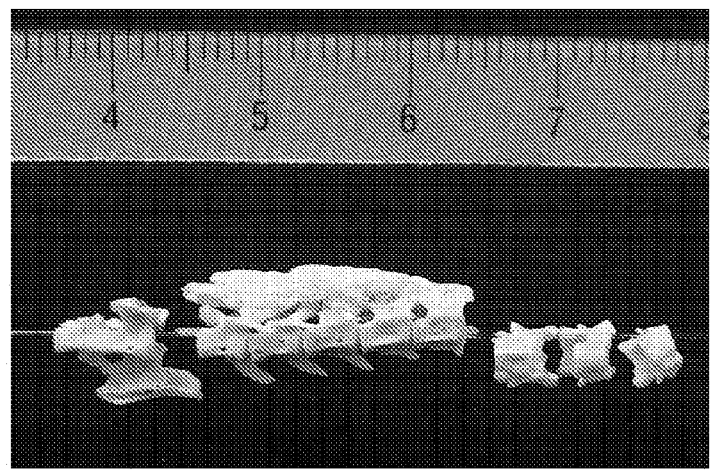
FIG. 6 illustrates the spine fusion that was observed in bones isolated from the mouse after induction of targeted heterotopic ossification. Associated soft tissues were removed by bleaching, leaving only the bone. Panel A shows a wire was threaded through the spinal column, to preserve the orientation of the vertebra. Unfused vertebrae hang free; fused vertebrae remain joined and rigid. Ruler is in millimeters. Radiographs of mouse spines 6 weeks after induction of spine fusion AdEmpty (Panel B) or AdBMP2 (Panels A, C) transduced cells. Panel A and C show obvious curvature of the spine suggesting a significant intentionally induced scoliosis, as compared to the normal mouse spine, shown in Panel B.
Figure 6:

Functional Demonstration of Fusion:

To further confirm spine fusion, the isolated spines used for mechanical testing were bleached to remove soft tissues, and analyzed on a gross level to see if the bone was contiguous. In particular, the bleached spines of the nine subjects confirmed fusion in all specimens, thereby demonstrating biomechanical constraint during mechanical testing. A representative 6-week spine shown in FIG. 6A shows five vertebrae of the lumbar spine are remodeled into a single structure. In all cases with biomechanical constraint of the spine after the induction of bone formation, there was also integration of the vertebra with heterotopic bone, which was observed after removal of the soft tissues. Cases that have not developed sufficient fusion confirmed the biomechanical findings because there was heterotopic bone that was not integrated with the vertebrae but rather formed individual bones in these cases.

Soft tissue removal and induced scoliosis demonstrate the fusion of the spine (FIGS. 6A, 6C). Representative radiographs show a distinct curvature of the spine towards the area of new bone formation and tentative fusion in animals receiving AdBMP2 transduced cells (FIG. 6C). This scoliosis has occurred in 6 month old growing mice in both immune competent and incompetent strains. This was observed in a large number of animals with heterotopic bone and tentative fusion, but absent in animals that received the control cells (FIG. 6B).

Accordingly, these results show that heterotopic bone can be rapidly induced by locally delivering high levels of BMPs using the delivery mechanisms of the present invention. The present invention demonstrates the ability of heterotopic ossification to form bridging bone and fuse adjacent vertebral bone without contribution from the skeletal bones. The results demonstrate that the present invention provides targeted heterotopic bone formation to a discrete location. That is, the present invention generates rapid heterotopic ossification that is fused and remodeled into two or more of the adjacent vertebra, reducing spine motion. The fusion appeared to be rapid, at a time scale of two weeks, and the new bone was limited in size and scale to regions of muscle which received the cells.

Histological analysis of this model demonstrate that the heterotopic bone grows into the skeletal bone with an organized growth plate, cortex, and tentative periosteum, similar to the vertebral bone. This process allows for the replacement of the cortical boundary with mature trabecular bone and bone marrow over time. The developed structures after 4 and 6 weeks are well fused both histologically and biomechanically.

Fusion of both the heterotopic bone to the skeletal bone and the resultant bridging of two vertebrae were rapidly achieved through simple injection. Within two weeks 44-100% of the spines in the two different murine models were considered fused by all criteria, radiological, histological, and biomechanical. In samples tested 4-6 weeks after induction, greater than 90% of all mice had achieved spine fusion in the two models and noticeable scoliosis was observed radiologically in the animals' spines suggesting that the fusion could restrain the spine, even during continued growth. The present invention provides clinically relevant spinal fusion in an animal model within 2 weeks through a single intramuscular injection without prior exposure and decortications.

Accordingly, the embodiments of the present invention are versatile, allowing any cell to be used as a delivery cell when adequate transduction with adenovirus is achieved. Thus qualified cell lines used in current clinical trials, such as mesenchymal stem cells, can be readily adapted for use in this cell based gene therapy system, making it very feasible to introduce clinically. The present invention provides for the fusing of the spine without surgical intervention, unlike current clinical approaches using recombinant BMP2 and other gene therapy approaches that require exposure of the vertebra and decortications, including harvesting autologous bone graft to use in place of ectopic bone, to induce bone growth and ultimately fusion of the skeletal bone to heterotopic bone. In particular, the present invention achieves spinal fusion with the creation of a bony fusion by means of the percutaneous injection of a biologically active material, without extensive surgical dissection and bony decortication.

EXAMPLE 2

Bone Formation with BMP Producing Cells Encapsulated in Hydrogel Microspheres Cell Culture Human diploid fetal lung fibroblasts (MRC-5) were obtained from the American Type Culture Collection (ATCC; Manassas, Va.) and propagated in a humidified incubator at 37° C. and 5% $CO_2$ in Dulbecco's Modified Eagle's Medium (DMEM; Sigma, St. Louis, Mo.) supplemented with 10% fetal bovine serum (FBS; HyClone, Logan, Utah), 1000 U/L penicillin, 100 mg/L streptomycin, and 0.25 µg/ml amphotericin B (Invitrogen Life Technologies, Gaithersburg, Md.), as described in Fouletier-Dilling, C. et al. Efficient and Rapid Osteoinduction in an Immune-Competent Host. *Human Gene Therapy* 18, 733-745 (2007). Murine bone marrow stromal cells (W20-17; a gift from Genetics Institute, Cambridge, Mass.) were propagated and maintained as described by Thies, R. Recombinant human bone morphogenetic protein-2 induces osteoblastic differentiation in W-20-17 stromal cells. *Endocrinology* 130, 1318-1324 (1992).

Adenoviruses and Cell Transduction

Replication-defective E1-E3 deleted first generation human type 5 adenovirus (Ad5) were constructed to contain cDNAs for BMP2 in the E1 region of the virus. Replication-defective human adenovirus type 35 fiber (Ad5F35) were constructed to contain cDNAs for BMP2 in the E1 region of the virus. For the viruses Ad5BMP2, Ad5dsRED, and Ad5empty cassette, the viral particle (VP)-to-plaque-forming unit (PFU) ratios were 1:83, 2, and 111 respectively, and all viruses were confirmed to be negative for replication-competent adenovirus. MRC-5 cells were transduced as previously described with Ad5BMP2, Ad5dsRED or Ad5empty cassette at a viral concentration of 2500 VP/cell. Briefly, virus was added to fresh supplemented DMEM and incubated with cells at 37° C. overnight.

Microencapsulation

Figure 13:
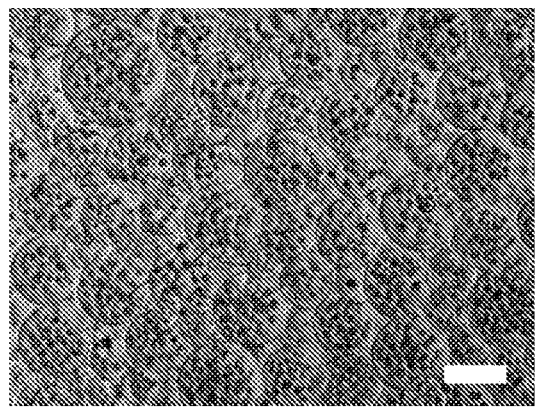
FIG. 13 shows an image of microencapsulated fibroblasts.

Hydrogel precursor solutions were formed by combining 0.1 g/ml 10 kDa PEG-DA (10% w/v) with 1.5% (v/v) triethanolamine/HEPES buffered saline (HBS, pH 7.4), 37 mM 1-vinyl-2-pyrrolidinone, 0.1 mM eosin Y, and transduced MRC-5 cells for a final concentration of $6 \times 10^4$ cells/µl. Acetophenone was combined in 1-vinyl-2-pyrrolidinone at a concentration of 300 mg/ml. The acetephenone was then added to mineral oil at 3 µl/ml and mixed well. The microspheres were formed after adding the hydrogel precursor solution into the mineral oil, emulsifying by vortex for 2 s while continuously exposing to white light for an additional 20 s. FIG. 13 shows an image of microencapsulated fibroblasts.

Microspheres were isolated by two series of media washes and centrifugation at 1350 rpm. Cells and microspheres were quantified by measuring the amount of soluble formazan produced by cellular reduction of the tetrazolium compound [3-(4,5-dimethylthiazol-2-yl)-5-(3-carboxymethoxyphenyl)-2-(4-sulfophenyl)-2H-tetrazolium, inner salt; MTS]. Briefly, cells were counted with a coulter counter and a serial dilution was used as a standard curve. Microsphere and cell samples were plated in a 24-well plate with 1 ml of culture medium and 200 µl of CellTiter 96® AQueous One Solution Reagent was added into each well of the plate. The plate was incubated for 1 hour at 37° C. in a humidified, 5% $CO_2$ atmosphere and then the absorbance was recorded at 490 nm in a plate reader. These microspheres were stable following intramuscular injection, as determined by retrieval of the microspheres post-injection to confirm that the majority of the microspheres remained intact. Further, to ensure proper comparisons between the microspheres and the monolayer cells we measured the loss of cells following the encapsulation procedure and loss in the injection needle. At minimum, 20% of the cells are entrapped within microspheres during the encapsulation process. This is accounted for so that equal cell numbers are delivered between 'direct injection' and 'microencapsulated' groups.

Preparation of Cells for Intramuscular Injection

Cells transduced with Ad5BMP2, Ad5dsRED, or Ad5empty cassette were removed with trypsin, and separated into two groups: one for direct injection and one for injection following microencapsulation. Cells directly injected were suspended at a concentration of $5 \times 10^6$ cells per 100 µl of PBS and aspirated into a syringe with a 22 gauge needle. Microencapsulated cells were encapsulated at a concentration of $5 \times 10^6$ cells per 300 µl of microspheres, which were in turn suspended in 1 ml of PBS and aspirated into a syringe with an 18 gauge needle. The greater volume of PBS and lower needle gauge enables the aspiration and injection of the microspheres, which would otherwise clog the needles.

Viability Assays

Cells were evaluated for their viability following microencapsulation. MRC-5 cells were transduced with Ad5F35BMP2, harvested and encapsulated in microspheres as described. One week after microencapsulation, microspheres were incubated with media and 2 μM calcein acetoxymethyl ester (calcein AM, Invitrogen, Inc.) for 20 min at 37° C. in a humidified, 5% $CO_2$ incubator. Microspheres were imaged under a confocal microscope (ex/em ~495 nm/~515 nm).

BMP-2 Quantification

BMP-2 expression was evaluated for MRC-5 cells transduced with Ad5F35BMP2 or Ad5F35HM4 using ELISA and alkaline phosphatase (AP) assays. ELISA assays were performed with a BMP-2 Quantikine ELISA kit from R&D Systems (Minneapolis, Minn.) using culture supernatant collected 72 hours after adenovirus transduction. Transduced cells were microencapsulated or plated directly in 0.4 μm pore polycarbonate membrane transwell inserts (Corning Inc., Lowell, Mass.) and W20-17 cells were cultured in the wells of 6-well plates. After 72 hours, W20-17 cells were assayed for AP activity using a chemiluminescence procedure. Cellular AP was extracted by conducting three freeze-thaw cycles on the W20-17 cells in a 100-μM/cm$^2$ concentration of 25 mM Tris-HCl (pH 8.0) and 0.5% Triton X-100. Then a ready to use chemiluminescent substrate disodium 3-(4-methoxyspiro {1,2-dioxetane-3,2-(5-chloro)tricyclo [$3.3.1.1^{3,7}$]decan}-4-yl)phenyl phosphate (CSPD) substrate with Sapphire-II enhancer (Tropix; Applied Biosystems, Foster City, Calif.) was added to the samples for enhanced AP sensitivity. The light output after a 2-sec delay was integrated from each sample for 10 sec with a luminometer (TD-20/20; Turner BioSystems, Sunnyvale, Calif.). AP levels were recorded in relative luminescence units (RLU). These AP levels were then normalized to protein content with the bicinchoninic acid (BCA) assay with bovine serum albumin as the standard curve. Data are presented as percent AP induction relative to that of basal control cells not exposed to BMP-2. Statistical analysis was performed as described in Fouletier-Dilling, C. et al. Efficient and Rapid Osteoinduction in an Immune-Competent Host. *Human Gene Therapy* 18, 733-745 (2007). Briefly, all data were taken in triplicate and reported as mean and standard deviation. A Student t test with 95% confidence interval (p<0.05) was done between the untreated control and each experimental condition.

Live Animal Optical Fluorescence Imaging

Mice were imaged longitudinally for approximately one month post-injection of microencapsulated or un-encapsulated fibroblasts transduced with Ad5dsRED (2500 vp/cell). Fluorescent imaging was performed at excitation and emission wavelengths of 568 nm and 590±10 nm, respectively. The excitation light was supplied by a 200 W Argon/Krypton laser, and the emission light was collected by passing through holographic and bandpass filters, and then focused onto an electron-modulated charge-coupled device (EMCCD) camera using a Nikkon camera lens. Exposure times were approximately 200 ms. Image analysis was performed using ImageJ software. Fluorescence intensity (FI) was measured and recorded for a region of interest (ROI) for each site of the animal injected with cells. The ROI dimensions were kept constant for every site imaged and each ROI was chosen to include the optimal fluorescent signal for the given site. A target to background ratio (TBR) of FI was calculated for each site by subtracting a background (B) ROI from the target (T) ROI, and then dividing the result by the background (B) ROI; TBR=(T−B)/B. The TBR value was plotted versus time (i.e., day post-injection of cells). Results represent the mean TBR of FI for unencapsulated and/or encapsulated Ad5dsRed or Adempty cassette transduced cells (n=4 per group). Statistical analyses were performed using the Student's t-Test, unpaired.

Heterotopic Bone Assay

Microencapsulated or unencapsulated cells were collected in syringes then delivered by intramuscular injection into the hind limb quadriceps muscle of nonobese diabetic/severely compromised immunodeficient (NOD/SCID) female mice (8-12 weeks old; Charles River Laboratories; Wilmington, Mass.) (n=6). Animals were euthanized two weeks after injection of the transduced cells. Hind limbs were harvested and placed in formalin. All animal studies performed were in accordance with an Institutional Animal Care and Use Committee (IACUC) approved protocol.

Histological Analysis

Harvested mouse hind limbs were fixed in formalin and decalcified. Hind limbs were then divided longitudinally and sectioned from the inner surface outward. Serial sections (5 μm) encompassing the entire hind limb reactive site were prepared (approximately 15-30 sections per tissue specimen). Every fifth slide was stained with hematoxylin and eosin to locate the region of interest. All tissue images presented in this report are representative of the other tissues isolated within the groups. All sections were analyzed by light microscopy.

Microcomputed Tomography

Micro-CT exams were obtained of the left and right legs at 15 μm resolution (eXplore Locus SP; GE Healthcare, London, ON, Canada). A hydroxyapatite phantom was scanned alongside each specimen and was used to convert the scan data from arbitrary units to units of equivalent bone density. A 3D region-of-interest was defined for each specimen to isolate the new mineralized tissue from the normal skeletal structures (femur, tibia, patella). The scans were threshold to exclude any tissue with a density less than 100 mg/cc, and the tissue volume within the region of interest was calculated as a measure of the total amount of mineralized tissue. The tissue mineral content was measured as an estimate of the total mineral in the region and the tissue density was calculated to quantify the density of the mineralized tissue. The resulting data were analyzed by one-way analysis of variance to identify any differences between the un-encapsulated and microencapsulated cells.

Validation of the Microsphere's Containing AdBMP2-Transduced Cells

Figure 7:
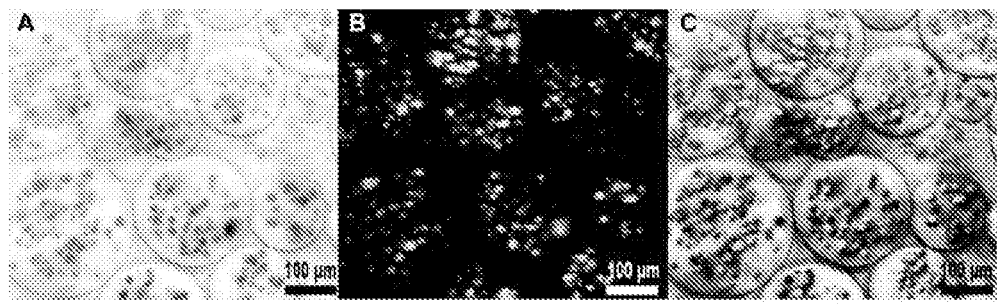
FIG. 7. Viability of AdBMP2-transduced cells (2500 vp/cell) within microspheres was assessed at day 7 using a LIVE/DEAD® Viability/Cytotoxicity Kit for mammalian cells (Invitrogen, Molecular Probes, Eugene, Oreg.). Panel A shows live cells appear green. Panel B shows dead cells appear red. Panel C shows the overlay of panels A and B. Living cells accounted for 95.08%±0.47% of total cells encapsulated.

In order to ensure that the cells tolerated encapsulation and that BMP-2 could freely diffuse out of the material; cells were microencapsulated and then stained using a Live/Dead cytotoxicity assay to determine the number and extent of viable cells within the PEG-DA hydrogel microspheres. With this method, live cells enzymatically convert non-fluorescent calcein acetoxymethyl (calcein AM) into fluorescent calcein, while an ethidium homodimer compound enters dead cells through damaged membranes and binds DNA to emit red fluoresence (FIG. 7). As seen in FIG. 7, cells that had been encapsulated within PEG-DA microspheres and placed in culture for seven days, showed high viability, 95.08%±0.47%, suggesting that the microencapsulation process was not leading to cell death.

Figure 8:
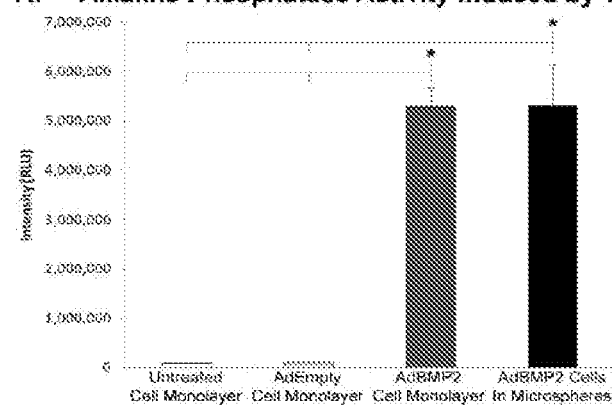
FIG. 8 shows a comparison of BMP-2 expression, secretion and activity after PEG-DA encapsulation. Panel A shows BMP-2 protein in culture supernatant taken from AdBMP2- or AdEmpty cassette-transduced cells (25000 vp/cell) (monolayer), or those encapsulated in PEG-DA microspheres was quantified daily over one week using an ELISA. Panel B shows alkaline phosphatase activity in W20-17 cells after addition of conditioned media from AdBMP2- or AdEmpty cassette-transduced cells (25000 vp/cell) (monolayer), or AdBMP2-transduced cells encapsulated in PEG-DA microspheres. As a negative control, the inventors also included culture supernatant from untransduced cells. Alkaline phosphatase activity is depicted as the average relative chemiluminescence units (RLU), where n=3. Error bars represent means±SD for n=3. A Student t-Test was applied to demonstrate significance and all the samples demonstrated significance at the confidence interval p<0.05.
Figure 8:
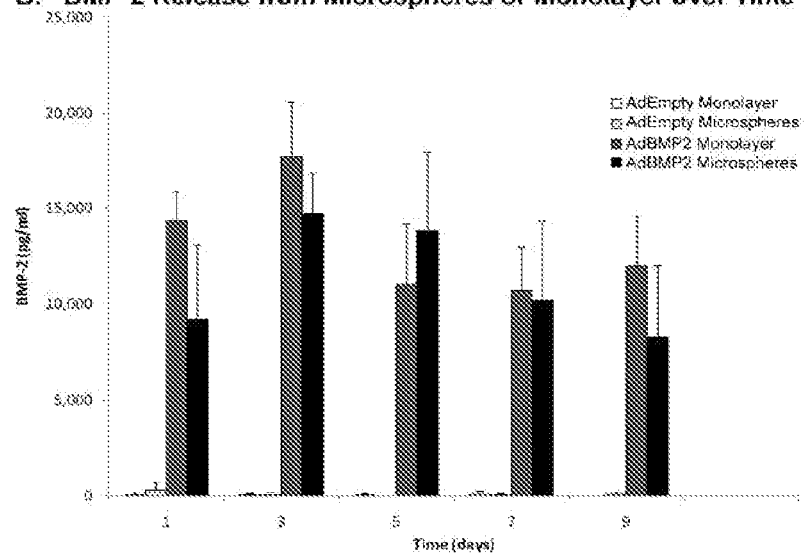

The level of BMP-2 in the culture supernatant was then measured to determine if the protein could adequately diffuse from the microspheres. Equivalent numbers of cells were transduced with AdBMP2 or AdEmpty cassette (2500 vp/cell) and either placed in culture directly, or after microencapsulation in PEG-DA microspheres. Culture supernatant was removed 72 hours later, and BMP-2 and its activity within the supernatants were quantified (FIG. 8). BMP-2 levels were quantified by ELISA and found to be approximately 17,500 pg/ml and 15,000 pg/ml of culture supernatant for directly plated and microencapsulated cells, respectively. No BMP-2 was detected in either culture supernatant from AdEmpty cassette-transduced cells, or control cells which had no additions. The inventors observed a significant drop in the level of BMP-2 production in larger bead structures as compared to equivalent numbers of cells either directly plated or in microspheres (data not shown). The data demonstrates that optimal BMP-2 production and secretion is achieved when cells are encapsulated into the smaller microsphere structures. Further, the data shows that the PEG-DA hydrogel material is not affecting the production, secretion or diffusion of BMP-2 within the microspheres (FIG. 8A).

The inventors also assayed BMP-2 activity in the culture supernatant to confirm that the protein that diffused through the PEG-DA hydrogel possessed similar specific activity as BMP-2 in culture supernatant from cells directly plated. The release of proteins from hydrogels is related both to diffusion distances and the hydrogel mesh size, both of which change with swelling. The hydrogels in this embodiment were formed with 10% 10 kDa PEG-DA, which has been estimated to have a mesh size of 280 Å. Proteins having radii smaller than the hydrogel mesh size enjoy relatively free diffusion through the polymer. Mature BMP-2 is a small protein (approximately 16 kDa) and it has been suggested that it dimerizes immediately after synthesis. The biologically active form of BMP-2 is a homodimer whose dimensions are 70 Å×35 Å×30 Å. Thus, BMP should pass freely through the microspheres. To confirm this result and ensure that the PEG-DA hydrogel microspheres were not selecting for a less active form of BMP-2, culture supernatants were tested in a cell-based functional assay. Culture supernatants were tested using the murine bone marrow stromal cell line, W20-17 cells, which have previously been shown to respond to functional BMP-2 by undergoing osteogenesis with a rapid increase in alkaline phosphatase (AP). W20-17 cells were exposed for 72 hours to a portion of the culture supernatants used for BMP-2 quantification and then cells were lysed for quantification of alkaline phosphatase (AP) activity (FIG. 8B). Both the culture supernatants from cells directly plated and encapsulated in microspheres led to significant elevation in alkaline phosphatase over the cells with no additions, demonstrating the BMP-2 is functionally active. Further, culture supernatant from cells which had been transduced with AdEmpty cassette did not elevate alkaline phosphatase significantly above the W20-17 cells with no additions (FIG. 8B). The data collectively demonstrate that microencapsulation of the cells in PEG-DA hydrogel does not significantly reduce the level of functional BMP-2 produced after transduction of the cells with AdBMP2.

In Vivo Comparison of Transgene Expression with and without Encapsulation in PEG-DA Hydrogel The cells were transduced with an adenovirus possessing the reporter gene dsRED or an empty cassette control virus to confirm that microencapsulation further prevents clearance of the transduced cells and extends transgene expression. This adenovirus was similar to the AdBMP2 virus; except that it possessed a dsRED cassette in place of the BMP-2, and cells were transduced in a similar manner. Cells ($5 \times 10^7$) were transduced with AddsRED (5000 vp/cell) and remained as a monolayer, or microencapsulated into microspheres, and 24 hours later directly injected into the muscle of the mouse hindlimb. As a control, $5 \times 10^7$ cells were transduced with AdEmpty cassette virus (5000 vp/cell) and then encapsulated into microspheres and similarly injected into mouse hindlimbs (n=4). Reporter expression within the tissues was then followed by live animal imaging for 2 to 34 days. Fluorescent imaging was performed at excitation and emission wavelengths of 568 nm and 590±10 nm, respectively. The excitation light was supplied by a 200 W Argon/Krypton laser and data were quantified and reported as a target to background ratio, where the specific signal was normalized to any background or autofluorescence.

Figure 9:
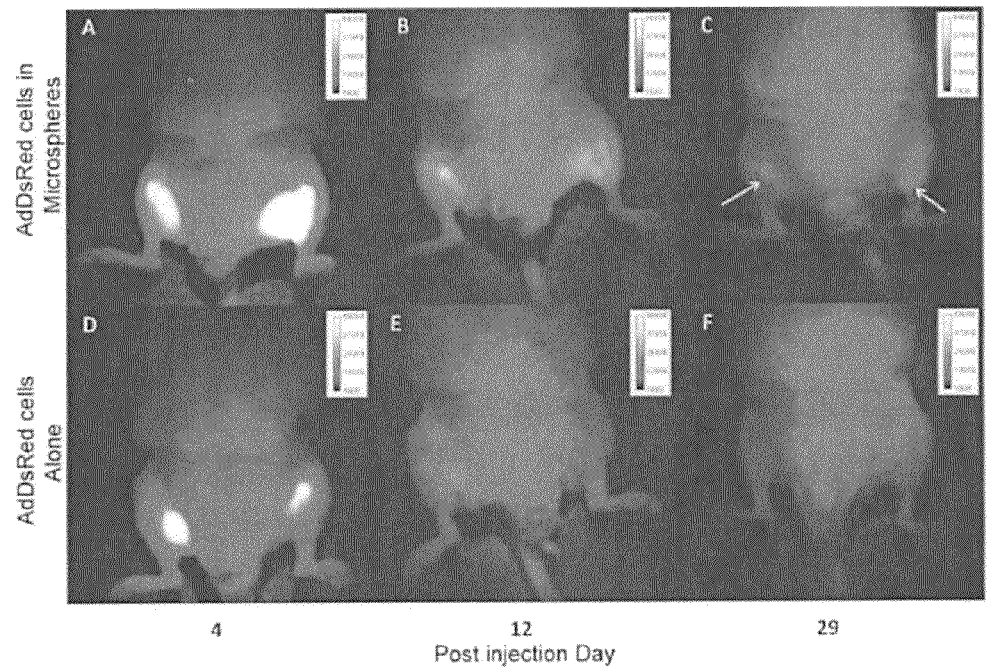
FIG. 9 shows an optical fluorescence imaging of mice injected with cells expressing dsRed. Top panels (A through C) are images of a representative mouse (n=4) injected with dsRed-expressing cells encapsulated in microspheres and bottom panels (D through F) are of a mouse injected with dsRed-expressing cells directly, without microspheres. The images were taken at day 4, 12 and 29 post-injection of cells. By day 29, the fluorescent signal is at background levels or undetectable for the mouse given dsRed-expressing cells without microspheres (panel F). Whereas, the signal remains detectable in the mouse given dsRed-expressing cells encapsulated in microspheres (panel C). Panel G shows the Mean Target-to-Background Ratio (TBR) of Fluorescence Intensity (FI) in mice given unencapsulated dsRed cells, microencapsulated dsRed cells or microencapsulated control cells. * p≤0.05 for microencapsulated dsRed cells versus microencapsulated control cells; † p≤0.05 for microencapsulated dsRed cells versus unencapsulated dsRed cells; ‡ p≤0.05 for unencapsulated dsRed cells versus microencapsulated control cells.
Figure 9:
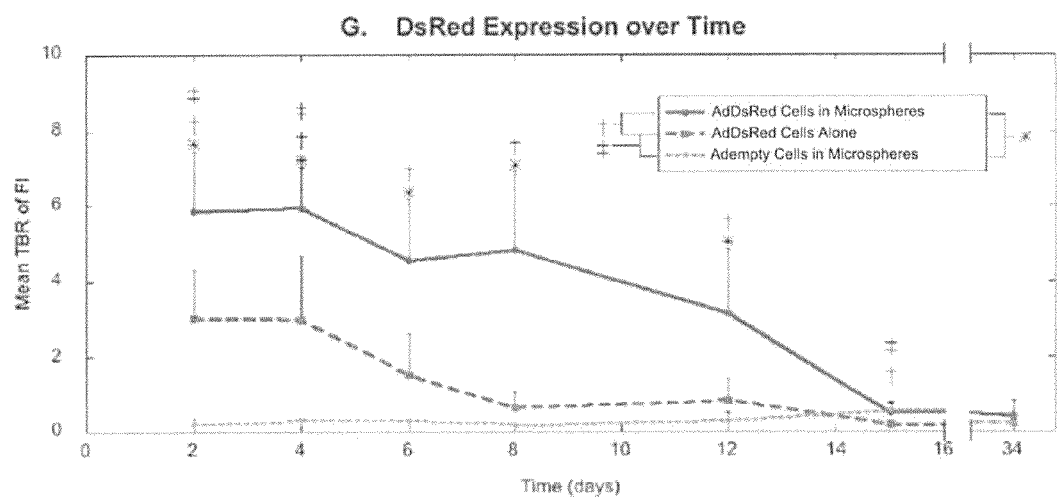

Two days after the initial injection of cells, dsRED expression was readily detected whether cells were encapsulated or not and in no cases were cells or microspheres detected migrating from the injection site. Because solution spread is a function of injection volume, dsRED expression in the tissues receiving the microspheres (FIG. 9A) encompasses a larger volume than the nonencapsulated counterpart (FIG. 9D). However, the magnitude of expression should not be affected by injection volume and dsRED expression was significantly elevated in microencapsulated cells (FIG. 9B) compared to directly injected cells (FIG. 9E). Reporter expression in animals receiving AdBMP2-transduced cells directly injected was substantially reduced after seven days and was indistinguishable from control (FIGS. 9E, 9G). The microencapsulated cells continued to be significantly elevated over background (FIG. 9B). This was not due to autofluorescence of PEG-DA indicated by the absence of signal at 590±10 nm in microencapsulated control cells. This 590±10 nm dsRED fluorescent signal was significantly elevated over that of microencapsulated cells transduced with AdEmpty cassette for 15 days (FIG. 9B). This demonstrates that the microencapsulated cells remained viable to express the dsRED transgene. Collectively, the data suggest that microencapsulation prolongs transgene expression within the tissues.

In Vivo Bone Formation with and without Microencapsulation in PEGDA Hydrogels

Figure 10:
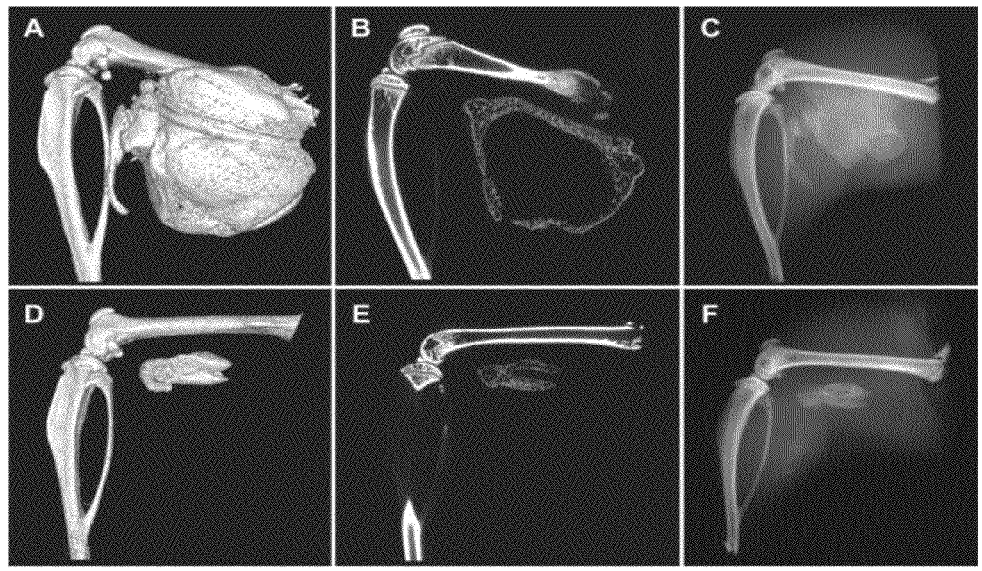
FIG. 10 shows the micro computational analysis of the resultant heterotopic bone formation. Top images (A, B) are 3D surface renderings of the resultant heterotopic bone, while bottom images (C, D) are cross-sectional slices through the new bone. Panels A and C show the resultant mineralization of the muscle tissues after injection of AdBMP2-transduced cells (2500 vp/cell) encapsulated into PEG-DA microspheres (panels A and C) or direct injection of unencapsulated AdBMP2-transduced cells (panels B and D). Both have a denser rim of bone, with a hollow interior structure, suggesting that the biomaterial did not alter bone patterning.

PEG-DA microspheres encapsulating AdBMP2-transduced cells were next tested in vivo to determine whether prolonged BMP-2 expression could enhance heterotopic bone formation. As with the live animal imaging, similar numbers of AdBMP2-transduced cells were either directly injected or following microencapsulation injected into the muscle in the mouse hind limb and the resulting heterotopic ossification was analyzed. MicroCT analysis of the resulting bone showed a significantly greater region or volume of heterotopic ossification in tissues receiving microspheres (FIGS. 10A-10C) than those receiving directly injected cells (FIGS. 10D-10F). Quantification of the groups (n=6) enabled direct comparison. Cross-sectional microCT analysis of the newly formed bone revealed a similar architecture between the two samples. Heterotopic bone formed by both the cells in microspheres, and the directly injected cells had a pattern of dense bone surrounding a hollow interior (FIGS. 10D-10F). While not shown, it is expected that animals that receive Adempty cassette transduced cells, whether encapsulated or not, do not show any heterotopic bone formation.

Figure 11:
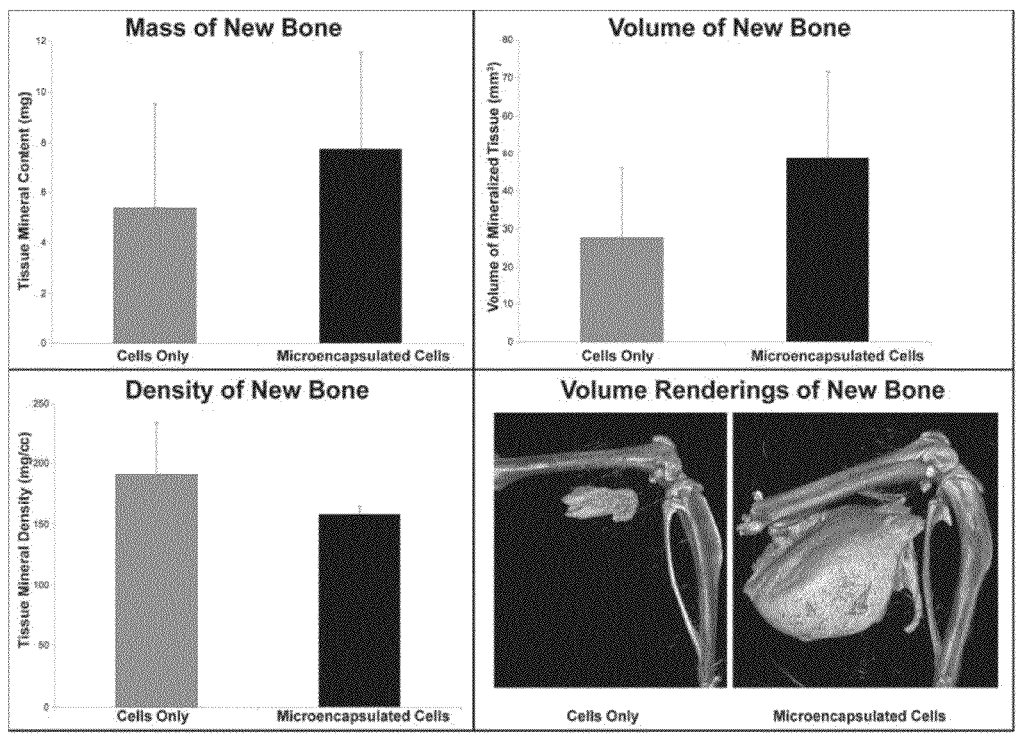
FIG. 11 shows quantification of the heterotopic ossification using microcomputational analysis. Cells were transduced with AdBMP2 and either directly injected or encapsulated into microspheres prior to injection, and the resultant heterotopic bone was analyzed two weeks later. Tissue parameters: Panel A shows bone tissue mineral content; Panel B shows bone volume of mineralized tissue, and Panel C shows bone tissue mineral density were calculated for the newly formed bone (n=6 per group). The means and standard deviations for each group were calculated and compared using a one-way analysis of variance. Results indicate that mineral content is statistically equivalent (p=0.2) between the groups, whereas the AdBMP2-transduced cells in microspheres had a significantly greater volume (p=0.038) than the AdBMP2-transduced cells directly injected. Alternatively, the bone tissue mineral density was significantly denser for the group receiving the cells directly as compared to those in microspheres (p=0.029). Panel D. shows a 3D volume rendering of new bone formed in cells only and microencapsulated cells, respectively.

Microencapsulated AdBMP2-transduced cells result in approximately twice the bone volume produced when these cells were directly injected (FIG. 11B). The bone tissue mineral content or mass of the new bone was statistically similar between these groups (FIG. 11A). Most likely the lack of statistical significance results from the change in tissue mineral density of the new bone (FIG. 11C). The new bone appears to be slightly less dense, leading to the overall similarity in mass.

Figure 12:
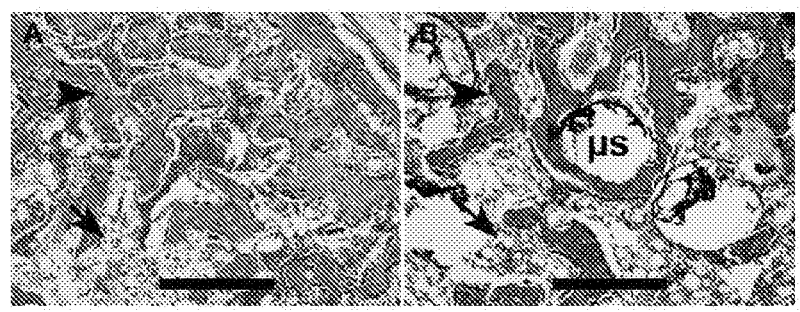
FIG. 12 shows photomicrographs of heterotopic ossification. Hematoxylin and eosin stains of new bone formation by direct injection (Panel A) and injection of microsphere encapsulated cells (Panel B). Both groups show small compact pieces of bone forming ring-like structures, encircling what appears to be blood and tentative stroma in the inner region, with significant adipose just exterior to the new bone. Scale bars are 500 μm.

To further analyze the newly formed bone, tissues were processed, paraffin embedded and the new bone was visualized by hematoxylin and eosin staining. Both groups had significant new bone formation within the muscle (FIG. 12). In tissues that had received the direct injection of AdBMP2-transduced cells, there was a small compact piece of bone forming a ring-like structure encircling what appears to be blood and tentative stroma, and just exterior to this structure was significant adipose (FIG. 12A). A similar structure was observed in tissues that had received microspheres (FIG. 12B). Since the microspheres do not degrade over time, they appear histologically as gaps or holes within the matrix (FIG. 12B). Thus, despite the presence of nondegradable microspheres, both structures were patterned to have a denser bone structure with a bone marrow-like cavity on the interior.

Microencapsulation further enhances the capability of the transduced cells of the present invention to induce bone formation. As such, microencapsulation provides local delivery of BMP via injection that avoids any required surgery to harvest the cells of the patient and prevents rapid clearance of the BMP or the cells from the injection site, and thereby extending the delivery of BMP to induce bone formation. Further, the microencapsulation of the present invention minimizes immune response to the polymer and does not bind BMP2. As such, unlike other carriers, the present invention does not limit any bioavailability of the produced BMP. In addition, the present invention is independent of cell line, permitting the transduction of any type of cell, and, with efficient transduction, delivering functional BMP continually to the target site over a prolonged period. Because the present invention provides for high transduction efficiencies, only a modest quantity of cells and microspheres is required for a therapeutic effect. For instance, in one embodiment, 300 µl of microspheres containing 2 million cells is used for injection. In some embodiments, the average radius of the microspheres is in the 50-150 µm range.

While in vitro cell survival between encapsulated and unencapsulated cells was comparable, in vivo cells protected within microspheres fared better than the directly injected counterparts. The duration of the dsRED fluorescence emitted from the microencapsulated cells demonstrates that microspheres are resistant to clearance and migration. Furthermore, microencapsulation does not interfere with the expression of the BMP-2 transgene. Cells in both monolayer and microspheres were able to make identical levels of functional protein. Since bone formation occurred immediately surrounding the microspheres, the area of new bone formation could easily be defined by the volume of material delivered. This is not true for the directly injected cells that stay tightly clustered, and will reside in adipose regions that can easily be compressed to hold the additional volume. Thus, the microencapsulation aspect of the invention provides for a more exact spatial placement of the transduced cells and produce bone of in a desired location and size. As such, the present invention can be implemented in the therapy to traumatic bone injury.

Further, spreading out the region in which BMP-2 is expressed through microsphere delivery resulted in a significant increase in the volume of bone, and decrease in bone density. In comparison, the cells directly injected which sit as a cluster within the tissues would produce the same amount of BMP-2 but in a much smaller volume, and resultant bone formation shows a small dense compact bone. Marrow-like structures formed in both the directly injected cells and the microencapsulated cells which were intriguing because in both cases the new structures possessed similar patterning to the normal skeleton. This demonstrates that despite the hydrogel's capacity to dictate the shape of the newly forming bone, it does not interfere with the structural patterning that is part of the biology of bone formation.

In alternative embodiments, hydrogels that are degradable by enzymes produced during bone formation may be used to address any interference of the hydrogel in the final bone density. Example 4 below demonstrates one embodiment of such degradable hydrogels. In particular, because the modified cells need immunoprotection only during the bone formation process, degradation of the hydrogel after the cells have served their purpose would be beneficial. Although there exist hydrolytically degradable hydrogel systems, the cathepsin K degradable polymer disclosed in Example 4 would be an improvement over such systems because degradation would be timed to the arrival of osteoclasts, and would proceed during the remodeling process of the newly formed bone. Hydrolytically degradable systems degrade at a set rate, purely dependent upon the water uptake. Because bone formation proceeds differently between each individual, a set rate that might be ideal in one animal or patient may not be appropriate for another. Thus, the rate of degradation should be set by the rate of bone remodeling. Cell mediated degradation is useful in any scenario where the presence of the hydrogel is needed until the host tissue has replaced it. When cell types other than osteoclasts are targeted for material degradation, one can easily change the peptide sequence in the polymer backbone to achieve sensitivity to other proteolytic enzymes. This approach could improve the design of tissue engineering scaffolds, wound dressings and other biomaterial devices.

EXAMPLE 3

Critical Size Bone Defect Repair with BMP Producing Cells Encapsulated in Hydrogel Microspheres Surgical Procedures All animal procedures were performed in accordance with the Institutional Animal Care and Use Committee of Baylor College of Medicine. Wistar rats were separated into groups receiving either autologous or microencapsulated allogeneic fibroblasts. Critical size femoral defects were created following exposure of rat femurs after linear incisions over the lateral aspect of the gluteal region from the palpable region of the greater trochanter of the femur to the knee. Once the aponeurotic fascia was separated, four end-threaded K wires were placed in the bone through the skin and Fessa external fixator was applied. Following fixation, an approximately 3.0 mm critical size defect was made through the incision with a 2 mm sterile tip surgical dremmel tool. The defect was injected with either 1) autologous cells transduced to express BMP-2; 2) autologous cells transduced with an empty virus; or 3) no treatment. Incisions were closed with surgical clips and antibiotic ointment was applied to closed incisions. Animals were given 0.05 mg/kg buprenorphine for pain and monitored until sternal recumbent.

Cell Culture, Transduction, and Microencapsulation

Fibroblasts were harvested from Wistar rat skin and expanded in DMEM supplemented with fetal bovine serum and gentomicin, penicillin and streptomycin. Expanded cells were transduced with replication defective E1-E3 deleted first generation human type 5 adenovirus (Ad5), which were constructed to contain cDNAs for human BMP2 in the E1 region of the virus. For the virus Ad5BMP2, the viral particle (VP)-to-plaque-forming unit (PFU) ratio was less than 1:500 and the virus was confirmed to be negative for replication-competent adenovirus. In certain embodiments, the PFU may be 1:77. Any virus that has a particle to PFU ratio greater than 1:500 is discarded.

Fibroblasts (1×10$^6$) were transduced with Ad5BMP2 at a viral concentration of 5000 VP/cell with 1.2% GeneJammer®, as described in C. M. Fouletier-Dilling et al., *Hum Gene Ther* 16, 1287 (November, 2005). Adenovirus-transduced Wistar skin fibroblasts were combined with 0.1 g/ml PEGDA with 1.5% (v/v) triethanolamine/HEPES buffered saline (HBS, pH 7.4), 37 mM 1-vinyl-2-pyrrolidinone and 0.1 mM eosin Y to form a hydrogel precursor solution. A hydrophobic photoinitiator solution (2,2-dimethoxy-2-phenyl acetophenone in 1-vinyl-2-pyrrolidinone, 300 mg/ml) was combined in sterile mineral oil (3 µl/ml). The cell seeded microspheres were formed after adding the hydrogel precursor solution into the mineral oil, emulsifying by vortex for 2 s while exposing to white light for an additional 20 s. FIG. 13 shows an image of microencapsulated fibroblasts. Microspheres were isolated by two media washes followed by 5 min centrifugation at 1350 rpm. These microspheres were collected and delivered via syringe into the femoral defect of Wistar rats.

In Vivo Repair of Critical Size Defects

To confirm that the microencapsulated BMP producing cells induce sufficient bone growth to repair a critical size defect of long bone, the inventors injected the autologous AdBMP2 transduced cells, AdBMP2 transduced allogeneic cells encapsulated in microbeads, or no cells into the defect. In this critical size defect model, the femur of the animal is cut, and a portion removed, to create a significant enough void that when fixed apart will not heal on its own, but rather progress to a non-union fracture. In particular, a 4-mm defect was introduced into the femur of several rats, and then an external fixation device applied by inserting two pins at the top and bottom of the bone ends. The pins were held in place by an external fessa or metal bar of consistent distance, to maintain the original length of the femur.

Figure 14:
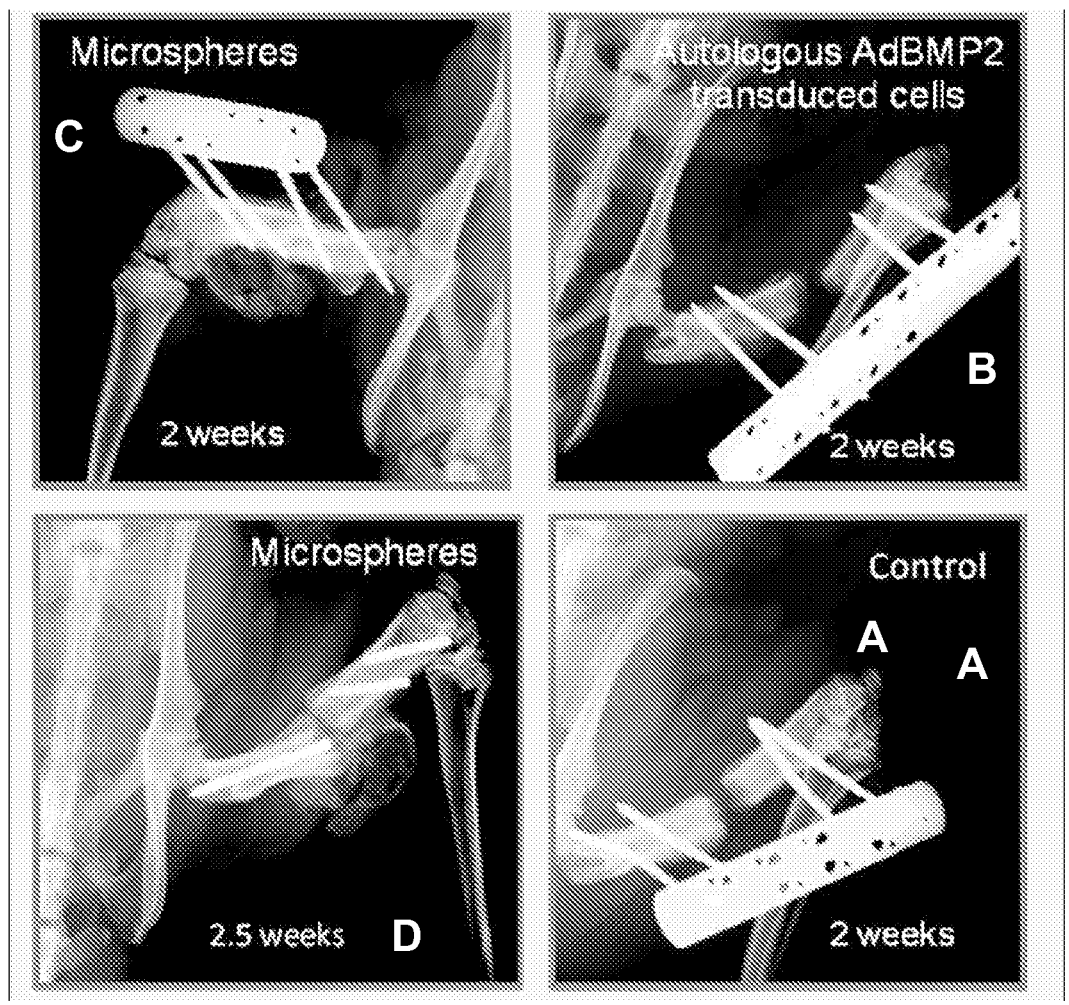
FIG. 14 shows radiographs of unrepaired critical size defects at 2 weeks post surgery. Panel A shows the control animal that received no treatment. Panel B shows the animal that received autologous AdBMP2-transduced fibroblasts. Panels C and D show animals that received allogeneic AdBMP2-transduced fibroblasts that were encapsulated into microspheres prior to injection.

The inventors then x-rayed the femurs approximately 2 weeks after induction of bone formation. As can be seen in FIG. 14C, there was substantial bone formation in the femoral defect receiving the allogeneic microbeads. The animals receiving the autologous cells did not show significant bone formation after two weeks (FIG. 14B). As expected the control also did not heal (FIG. 14A).

Subsequently, the inventors removed the external fixator in one of the two animals receiving allogeneic microbeads to determine if the newly forming bone was weight bearing. The animals was observed for two days around the clock, and then daily for the following week, and showed no signs of lameness, and continued to ambulate, feed and do other activities similar to normal rats. The inventors x-rayed the animals again at 2.5 weeks to ensure that there were no small fractures or compression of the new bone from the weight bearing activities (FIG. 14D). As can be seen in FIG. 14D, the distance between the skeletal bone ends, appears to be maintained, suggesting that no compression has occurred from the animal ambulating on the limb without additional fixation. In summary, animals in the autologous and control groups show no healing of the critical size defect at 2 weeks (FIG. 14A-B). In contrast, animals receiving microencapsulated AdBMP2-transduced allogeneic fibroblasts show robust bone growth at the 2 week time point (FIG. 14C-D).

Figure 15:
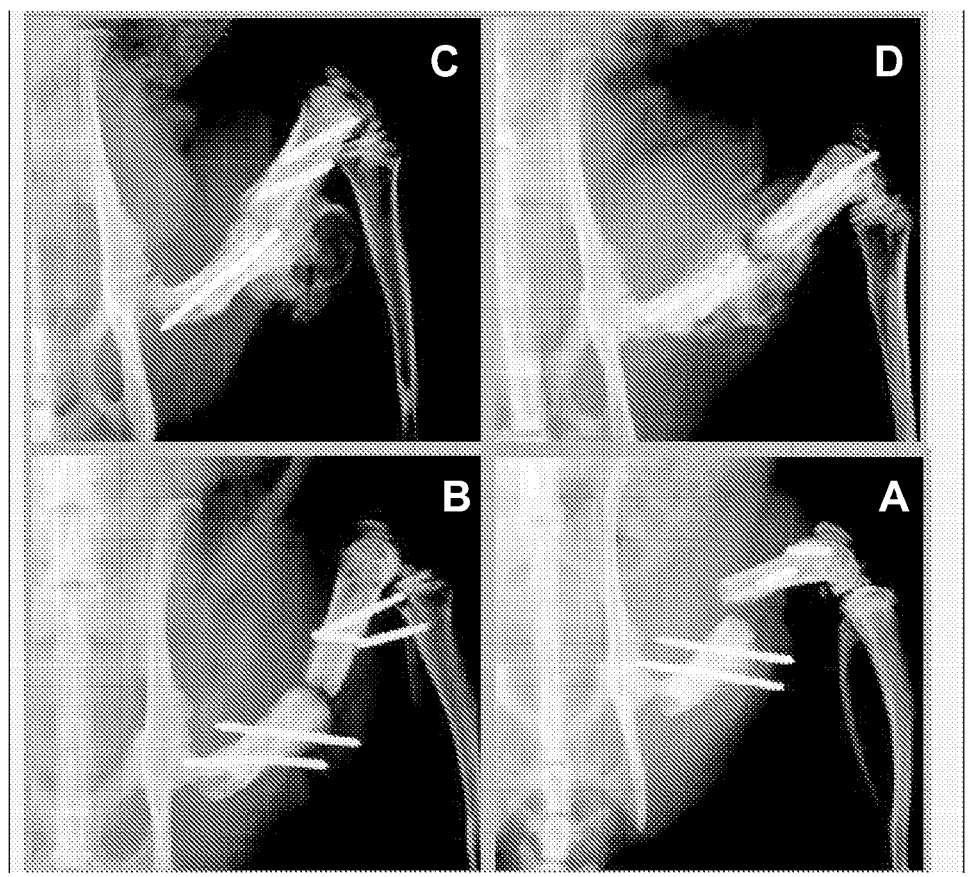
FIG. 15 shows radiographs of the rat femurs 3 weeks after introduction of the critical size defect into the rat femur. Panel A shows the control animal that received no treatment. Panel B shows the animal that received autologous AdBMP2-transduced fibroblasts. Panels C and D show animals that received allogeneic AdBMP2-transduced fibroblasts that were encapsulated into microspheres prior to injection. Animals were euthanized prior to radiographs.

The inventors also x-rayed all the animals at 3 weeks (FIG. 15). The bone of the newly formed bone in the animal which was allowed to bear weight was substantially more mineralized than the counterpart. Accordingly, in implementations involving critical size defects, the present invention provides for sufficient heterotopic ossification to heal a critical size defect in the femur of wild type rats; using AdBMP2 transduced allogeneic rat cells that are encapsulated into microbeads using PEGDA hydrogel. Bone formation was able to rapidly fill the defect, resulting in the animal being able to bear weight on the limb, without any apparent lameness as early as two weeks after introduction of the material. The animal continued to ambulate on the limb without external fixation for the duration of the experiment.

The present invention further provides the advantages of avoiding the use of free adenovirus within the organism and ensuring both efficient transduction of the cells and ultimately expression of the BMP transgene. The non-integrating approach of the present invention provides additional safety because the BMP transgene does not integrate into the chromosome. As such, the risk of disrupting other genes that may lead to altered cell growth is eliminated. Further, the encapsulation ensures that the transduced cells do not integrate into the newly forming bone. Encapsulation of the transduced cells further allows for an allogenic cell line to be efficacious, thus avoiding the need to harvest and prequalify patient cells. The transduced cells of the present invention have continued efficacy after cryopreservation, which greatly enhances the capability to clinically manufacture the material. The methods of the present invention, including microencapsulation of transduced cells, allow for targeted rapid bone formation. Consequently, the present invention offers treatment options for bone injuries and defects, such as traumatic injuries resulting in missing bone segments, injuries and defects requiring spinal fusion, limb lengthening applications, and other orthopedic applications which require bone formation at specific locations.

EXAMPLE 4

Encapsulation with Degradable Hydrogel Microspheres

Synthesis and Characterization of Acryloyl-PEG-Succinimidyl Carbonate (Acrylol-PEG-SMC)

All reagents were obtained from Sigma unless otherwise noted. 50 mM of poly(ethylene glycol) (PEG, 3,400 Da; Fluka, Milwaukee, Wis.) was reacted with 75 mM silver (I) oxide and 55 mM acryloyl chloride in anhydrous dichloromethane (DCM). Potassium iodine (30 mM) was added as a catalyst, and the mixture was reacted at 4° C. overnight. To purify the acryloyl-PEG-OH, silver (I) oxide was first removed by filtering the mixture through a Celite 521 pad (Spectrum Chemical Manufacturing Corp, Gardena, Calif.). For further purification, the filtrate was dried by using a Rotovap, re-dissolved in de-ionized water, and adjusted to pH 3 with 6 N HCl. After heating to 35° C. and venting to air for 1 h, activated charcoal (Fisher Scientific, Pittsburgh, Pa.) was added to the mixture and stirred overnight to absorb iodine. The charcoal was then removed via filtration. Sodium chloride (25% w/v) was dissolved in the aqueous filtrate followed by DCM extraction. The organic phase was collected and extracted again with 2 M potassium bicarbonate to remove chloride ions. Acryloyl-PEG-OH was recovered by precipitation in cold ethyl ether, filtered, dried under vacuum overnight, and lyophilized until completely dry. To proceed with the succinimidyl carbonate conjugation, 25 mM acryloyl-PEG-OH was mixed with 75 mM pyridine and 100 mM N,N'-disuccinimidyl carbonate in anhydrous acetonitrile. After reacting under argon overnight, pyridine and acetonitrile were removed with a Rotovap. The mixture was then re-dissolved in anhydrous DCM and filtered to remove unreacted N,N'-disuccinimidyl carbonate. Acetate buffer (0.1 M, pH 4.5, 15% NaCl) was then used for phase extraction. The organic layer was collected and then dried by anhydrous $MgSO_4$ Acryloyl-PEG-SMC was recovered following precipitation in cold ethyl ether, filtered, and dried under vacuum overnight. The products were analyzed by $^1$H-NMR (Advance 400, Bruker, Germany) and matrix-assisted laser desorption ionization time of flight mass spectrometry (MALDI-ToF; Bruker Daltonics, Billerica, Mass.) and stored at −80° C. under argon.

Synthesis and Characterization of Acryloyl-PEG-GPSG-PEG-Acryloyl, Acryloyl-PEG-RGDS, and Fluorescently-Labeled Acryloyl-PEG-RGDS Conjugates The cathepsin K-sensitive peptide sequence GGGMGPSGPWGGK (GPSG) was synthesized on an APEX 396 peptide synthesizer (Aapptec, Louisville, Ky.). The glycine spacers sandwiching the peptide were included to avoid steric hindrance with cathepsin K. Lysine was included for the free amine on its side chain, enabling reaction with the active esters in the heterobifunctional acryloyl-PEG-SMC. A tryptophan residue was incorporated into the peptide sequence for the purpose of tracking in vitro degradation by monitoring UV absorbance at 280 nm. After synthesis, the peptide was cleaved from the polystyrene resin (95% trifluoroacetic acid, 2.5% water, and 2.5% triisopropylsilane), precipitated in ethyl ether, and purified by dialysis. Following purification, the molecular weight of the synthesized peptide was confirmed with MALDI-ToF. The crosslinkable cathepsin K sensitive acryloyl-PEG-GGGMGPSGPWGGK-PEG-acryloyl (acryloyl-PEG-GPSG-PEG-acryloyl) polymer was synthesized by reacting the peptide with acryloyl-PEG-SMC in a 2.1:1 (PEG:peptide) molar ratio in 50 mM sodium bicarbonate buffer (pH 8.5) at room temperature overnight. The product was dialyzed, lyophilized, and stored under argon at −20° C. until use. The cell adhesive peptide Arg-Gly-Asp-Ser (RGDS, American Peptide, Sunnyvale, Calif.) was also reacted with acryloyl-PEG-SMC in a 1.1:1 molar ratio to give acryloyl-PEG-RGDS. Conjugation products were analyzed by $^1$H-NMR and gel permeation chromatography (GPC; Polymer Laboratories, Amherst, Mass.) with UV/Vis and evaporative light scattering detectors. Fluorescently labeled acryloyl-PEG-RGDS was synthesized as previously describe. In brief, purified acryloyl-PEG-RGDS was mixed with Alexa Fluor 680 carboxylic acid (Invitrogen, Carlsbad, Calif.) in 50 mM sodium bicarbonate buffer in a 1:10 (acryloyl-PEG-RGDS:dye) molar ratio and allowed to react for 1 h at room temperature. The desired products were then purified by a Sephadex G-25 fine chromatography column (Amersham Bioscience, Uppsala, Sweden) followed by dialysis and lyophilization. Recovered products were stored under argon at −20° C. until use.

In Vitro Degradation Profiles of the PEG-GPSG Hydrogel

The degradation profiles of PEG-GPSG hydrogels were measured by monitoring the release of tryptophan into solution after incubation with different enzymes. A pre-polymer solution was prepared by combining 0.1 g/ml crosslinkable acryloyl-PEG-GPSG-PEG-acryloyl with 1.5% (v/v) triethanolamine, 37 mM 1-vinyl-2-pyrrolidinone, and 1% (v/v) of 1.0 mM eosin Y in tris buffered saline (TBS; pH 7.5, 10 mM $CaCl_2$, 0.1% Tween 20, 0.2 mg/ml sodium azide). The precursor solution was sterilized by filtration using a 0.22 µm filter (Millpore Corporation Bedford, Mass.). For in vitro enzyme degradation tests, 3 µl of pre-polymer solution was transferred to the bottom corner of a micro-cuvette (Brandtech, Essex, Conn.) and polymerized by exposing to visible light for 2 min. Following equilibrium swelling overnight in 250 µl TBS, each hydrogel was incubated with 250 µl enzyme solution at 37° C. for 24 h. Proteinase K (Invitrogen), plasmin, type I and type III collagenase (COL I and COL III; Worthington, Lakewood, N.J.) were prepared in TBS to a final concentration of 0.05 mg/ml. Procathepsin K (Enzo Life Science, Plymouth Meeting, Pa.) was first activated in 35 mM sodium acetate (pH 3.5) for 2 h at room temperature. Activated cathepsin K was then adjusted to 0.05 mg/ml in 50 mM sodium acetate buffer (NaOAc; pH 5.5, 2.5 mM EDTA, 1 mM DTT, 0.01% Triton X-100, 0.2 mg/ml sodium azide). Hydrogels were also incubated in TBS and NaOAc buffer as negative controls. Degradation was evaluated by measuring the absorbance change at 280 nm of test solutions to monitor the release of tryptophan over time with a UV/Vis spectrophotometer (Carey 50, Varian, Palo Alto, Calif.).

Cell Maintenance of MC3T3-E1 and RAW 264.7 Cells

Murine pre-osteoblast cells MC3T3-E1 subclone 4 and macrophage cells RAW 264.7 (ATCC, Manassas, Va., USA) were cultured in alpha-MEM medium (Gibco BRL, Canada) and DMEM (ATCC), respectively. Culture media were supplemented with 10% fetal bovine serum (FBS; Atlanta Biologicals, Lawrenceville, Ga.), 100 U/ml penicillin, and 100 mg/ml streptomycin (Gibco BRL, Canada). Cells were incubated at 37° C. with 5% $CO_2$. The media were refreshed every 2-3 d and confluent cells were subcultured through trypsinization for MC3T3-E1 and scraping for RAW 264.7. All experiments were conducted using cells between passages 4-10. MC3T3-E1 cells were differentiated into osteoblasts via supplied 50 µg/ml ascorbic acid and 10 mM b-glycerophosphate to the growth medium. Differentiation medium was subsequently replaced every 2-3 d. To differentiate cells to multinuclear osteoclasts, RAW 264.7 were seeded at a density of $1.5 \times 10^5$ cells/cm$^2$ and allowed to adhere for 4 h. Culture media was then supplemented with 30 ng/ml of receptor activator of nuclear factor kappa B ligand (RANKL; R&D Systems Inc., Minneapolis, Minn.) and replaced every 2 d. The cells were cultured for an additional 4 d before further use.

Serum Gradient Purification of Differentiated Multinuclear RAW264.7

Differentiated multinuclear RAW264.7 (dRAW264.7) were purified by a serum gradien. After differentiation in culture medium supplemented with 30 ng/ml RANKL for 4 d, dRAW264.7 cells were trypsinized and resuspended in 15 ml of Moscona's high carbonate (MHB; pH 7.2, 137 mM NaCl, 2.7 mM KCl, 0.4 mM $NaH_2PO_4$, 12 mM $NaHCO_3$, and 11 mM dextrose) solution. A serum gradient was prepared by placing a layer of 15 ml 70% FBS solution in MHB at the bottom of a 50 ml conical tube, and then slowly overlaying with a second layer of 15 ml 40% FBS solution. Fifteen ml of cell suspension was then slowly added to the top without disturbing the layers. The tube was then capped and held undisturbed at room temperature for 30 min to permit cells to separate based on size. The top 17 ml layer, middle 16 ml layer, and bottom 12 ml layer were collected separately. Cells in each layer were centrifuged at 500×g for 5 min, resuspended in culture medium, and seeded in 12 well tissue culture plates at a density of 5,000 cells/cm$^2$ overnight. In order to confirm the presence of differentiated osteoclasts, cells were then stained for the activity of tartrate-resistant acid phosphatase (TRAP) as previously described. Briefly, after fixing cells in 4% formaldehyde, TRAP staining solution was prepared containing 0.125 mg/ml Naphthol AS-BI Phosphate, 0.1 M acetate buffer, 6.7 mM L(+)-tartrate, 1 mM sodium nitrite, and 0.07 mg/ml diazotized fast garnet GBC. Media was aspirated and 1 ml of TRAP staining solution was added to each well. After staining at 37° C. for 1 h, each well was rinsed three times with deionized water and allowed to air dry before imaging.

Surface Degradation of Differentiated RAW 264.7 and MC3T3-E1 on PEG-GPSG Hydrogels Flat hydrogel sheets for surface degradation studies were formed by adding 10 mM acryloyl-PEG-RGDS and 1 mM Alexaflour 680 labeled acryloyl-PEG-RGDS to the PEG-GPSG pre-polymer mixture (0.1 g/ml acryloyl-PEG-GPSG-PEG-acryloyl with 1.5% (v/v) triethanolamine, 37 mM 1-vinyl-2-pyrrolidinone, and 1% (v/v) of 1.0 mM eosin Y in tris buffered saline) and polymerizing between a mica sheet (Ted Pella, Inc., Redding, Calif.) and glass slide separated by a 1 mm Teflon spacer. The mica sheet resulted in hydrogels with atomically smooth surfaces. Both MC3T3-E1 and RAW 264.7 cells were differentiated for 4 d in differentiation media in tissue culture plates. Differentiated MC3T3-E1 (dMC3T3-E1) were subcultured and seeded on to the atomically smooth hydrogel surfaces at a density of $5 \times 10^4$ cells/cm$^2$. Differentiated multinuclear RAW264.7 osteoclasts collected at the bottom layer of the serum gradient were also seeded on smooth hydrogel surfaces at the same density. Hydrogels seeded with either osteoblasts or osteoclasts were then cultured in differentiation medium for 48 h before further analysis.

Confocal Microscopy of Pit Formation on Cathepsin K Sensitive PEG Hydrogel Surfaces Following 48 hours of incubation, hydrogel surfaces were imaged after cells were either removed by 20 mM EDTA, or fixed and stained with 4',6-diamidino-2-phenylindole (DAPI; Invitrogen) and rhodamine phalloidin (Invitrogen). Differential interference contrast (DIC) or fluorescence images were taken by LSM-5 LIVE microscope systems (Carl Zeiss Inc., German). Z-stack images were acquired with a 20× objective. The z distance between each step was 0.253 µm. Images were all processed with ImageJ 142 (NIH, Bethesda, Md.). Three dimensional image reconstructions were processed using OsiriX Medical Imaging software (version 3.0.2; the OsiriX Foundation, Geneva, Switzerland).

In Vitro Degradation of Cathepsin K-Sensitive PEG-GPSG Hydrogels

Figure 17:
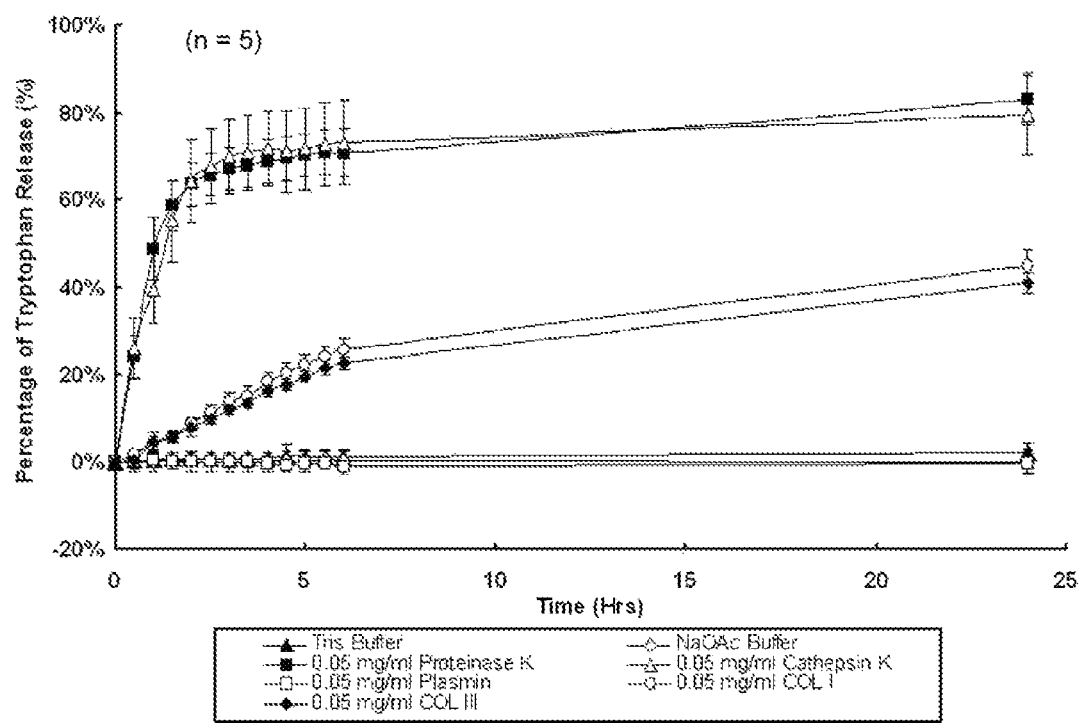
FIG. 17 shows degradation profiles of cathepsin K-sensitive GPSG hydrogels. Hydrogel droplets (3 μl) were polymerized in each micro-cuvettes and swelled overnight with 250 μl of TBS buffer. Each hydrogel was incubated in buffer or enzyme solution at 0.05 mg/ml at 37° C. UV absorbance at 280 nm was measured over 24 hours to monitor tryptophan release corresponding to the degradation of the GPSP hydrogels.

The tryptophan incorporated in the GGGMGPSGPWGGK peptide allowed detection of enzymatic cleavage of the PEG-GPSG hydrogels by monitoring the release of tryptophan into solution. After incubation in different enzyme solutions for 24 h, hydrogels in cathepsin K and proteinase K solutions had similar degradation profiles, both indicating a rapid tryptophan concentration increase within the first hour and reaching about 80% release of total tryptophan at 24 h (FIG. 17). No degradation was observed when hydrogels were incubated in TBS buffer, NaOAc buffer, or plasmin. Hydrogels incubated in nonspecific collagenase I and collagenase III solutions also released 40% of incorporated tryptophan after a 24 h incubation.

Differentiation of RAW264.7

Figure 16:
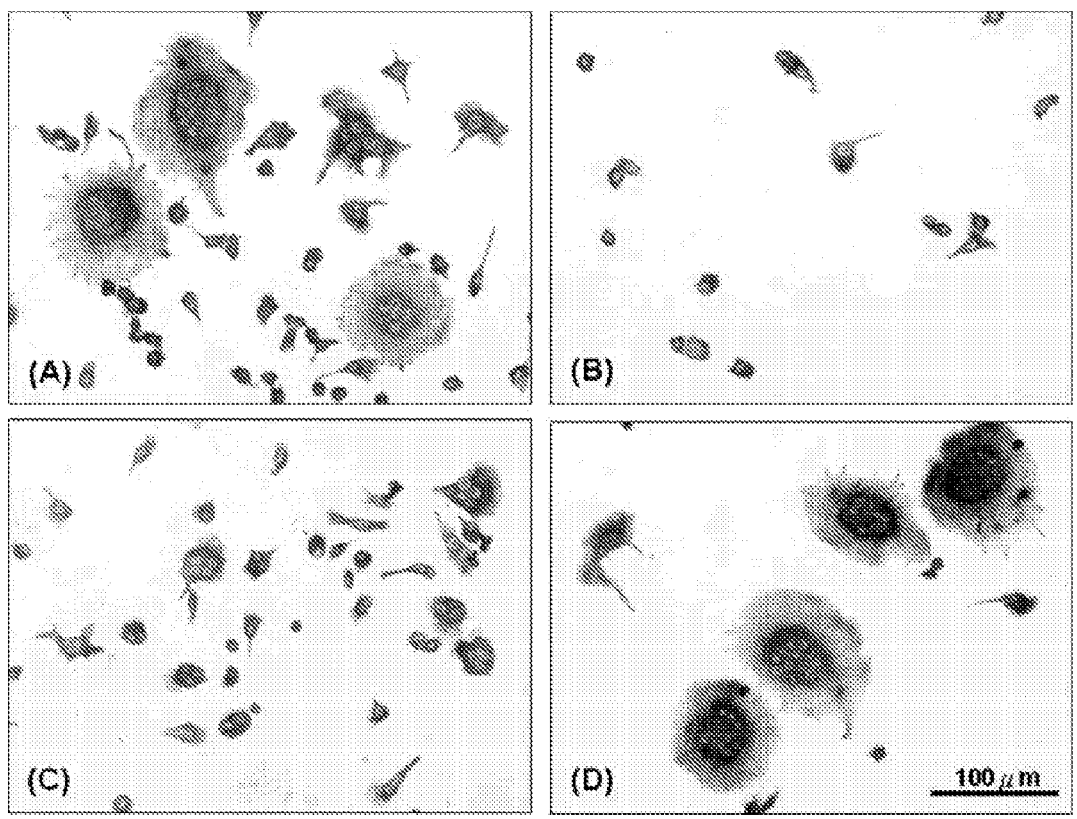
FIG. 16 shows isolated TRAP-positive dRAW264.7 osteoclasts by serum gradient. After differentiation in medium containing 30 ng/ml RANKL for 4 days, dRAW264.7 cells were combined with mono- and multi-nuclear cells (FIG. 15A). After separation by serum gradient, the top fraction contained most of the mononuclear cells. The middle fraction of the gradient contained mixed groups of mononuclear and multinuclear cells. The majority of cells at in the bottom fraction were multinuclear cells, which contained a very small portion of mononuclear cells (FIGS. 15B-D). The multinuclear cells collected at in the bottom fraction were also stained TRAP positive, which indicated that they were activated osteoclasts. The bottom fraction of TRAP+dRAW 264.7 osteoclasts were was then used for hydrogel degradation studies.

RAW264.7 cells stained for TRAP activity were all negative prior to incubation with RANKL and all positive afterwards. Although all RANKL exposed RAW264.7 cells stained TRAP positive, not all of these cells fused into multinuclear cells (FIG. 16A). After separation by serum gradient, the top fraction of the gradient contained most of the mononuclear cells. The middle fraction of the gradient contained mixed groups of mononuclear and multinuclear cells. The majority of cells in the bottom fraction were multinuclear cells and contained a very small portion of mononuclear cells (FIGS. 16B-D). The multinuclear cells collected in the bottom fraction also stained TRAP positive, which indicated that they were differentiated multinuclear osteoclasts.

DIC Images of Cathepsin K Sensitive Hydrogel Surfaces Seeded with dMC3T3E1 and dRAW264.7

No features were detected on hydrogel surfaces seeded with dMC3T3-E1 osteoblasts. On hydrogel surfaces seeded with dRAW264.7 osteoclasts, several features were observed after cells were detached. The intensity profile of the DIC image suggests that the features on the hydrogels were depressions (not shown).

Three Dimensional Image Reconstruction of dRAW264.7 Cells on the Surface of Cathepsin K Sensitive Hydrogels dRAW264.7 cells stained with DAPI and rhodamine phalloidin showed multinuclear, polarized cells on the hydrogel surface (not shown). A sealing ring of F-actin and multiple nuclei were clearly observed. Beneath the hydrogel surface where an osteoclast was located, a decrease in the hydrogel's fluorescent signal was observed. Three dimensional volume reconstructions of z-stack images further illustrate this fluorescent signal loss by showing it as a hole in the hydrogel through which the cell can be visualized (not shown). This signal loss is indicative of activity by the differentiated RAW264.7 osteoclasts, degrading the underlying hydrogel and creating a characteristic resorption pit, resulting in the fluorescent intensity loss. No signal loss was observed on the hydrogels seeded with dMC3T3-E1 cells (not shown).

The present invention provides for synthesis of an osteoclast degradable hydrogel. In particular, the present invention provides a synthetic polymer with high sensitivity and specificity for cathepsin K by incorporating the collagen I ($\alpha$-1) peptide fragment. Enzyme degradation experiments establish that both the peptide fragment and polymerized hydrogel are degradable by cathepsin K, whereas nonspecific collagenases only have a moderate effect. Cell culture experiments demonstrated that osteoclasts are capable of binding to and degrading an RGDS-modified version of this hydrogel. When seeded with osteoblasts or osteoclasts, these hydrogels showed evidence of degradation only on surfaces seeded with osteoclasts, which revealed characteristic resorption pits, further demonstrating that degradation of the polymer is both enzyme and cell specific. In particular, the degradable hydrogel of this embodiment is specific to the enzymes and cells with key roles in bone resorption. Accordingly, the present invention provides for the synthesis of degradable hydrogels based on the properties of bone resorption and remodeling.

EXAMPLE 5

Dosage Response

Cell Culture

A human fibroblast cell line (MRC5) was acquired from the American Type Culture Collection (Manassas, Va.) and propagated in Dulbecco's modified Eagle's medium (DMEM). The medium was supplemented with 10% fetal bovine serum (Hyclone, Logan, Utah), penicillin (100 units/mL), streptomycin (100 µg/mL), amphotericin B (0.25 µg/mL) (Invitrogen Life Technologies, Gaithersburg, Md.) and tetracycline (3 mg/L) (Sigma, St. Louis, Mo.). MRC5 cells are not capable of inducing bone formation before transduction. W20-17, a murine stromal cell line, was obtained as a gift from Genetic Institute, Cambridge, Mass. and was propagated as described by [Thies et al., 1992]. The W20-17 cells were briefly grown in supplemented DMEM and cultured at a subconfluent density in order to maintain the phenotype. All cell types were grown at 37° C. and 5% $CO_2$ in humidified air.

Adenovirus Transduction

A replication-defective E1-E3-deleted human adenovirus type 35 fiber protein (Ad5F35) were constructed to contain cDNAs for BMP2 in the E1 region of the virus or did not contain any transgene in this region, AdEmpty. The resultant purified viruses, AdBMP2 and AdEmpty cassette, had viral particle (VP)-to-plaque-forming unit (PFU) ratios of 1:77 and 1:111 respectively, and all viruses were confirmed to be negative for replication-competent adenovirus. Cells were transduced as previously described with AdBMP2 or AdEmpty cassette at a viral concentration of 2500 VP/cell. MRC5 cells were transduced with either AdEmpty or AdBMP2 in DMEM supplemented with 2% FBS at a concentration of 2500 viral particles per cell. Adenovirus was allowed to incubate overnight at 37° C., humidified atmosphere, 5% $CO_2$.

Quantification of BMP2

BMP2 protein was measured in culture supernatant taken from cells 72 hours after transduction with AdBMP2 and culture supernatant was collected and assayed for BMP2 protein using a Quantikine BMP2 immunoassay ELISA kit (DBP200; R&D Systems, Minneapolis, Minn.). BMP2 protein activity was quantified in culture supernatant collected from cells after transduction with AdBMP2 or AdEmpty cassette or no virus, and a portion incubated with W20-17 bone marrow stromal cells, which rapidly increases alkaline phosphatase expression. Alkaline phosphatase activity is readily quantified. Briefly, W20-17 cells were plated in 24 well plates at subconfluent densities ($5 \times 10^4$ cells/cm2) and 24 hours later the media was replaced with 200 µL of fresh media and 200 µL of conditioned culture media from various cells doses. W20-17 cells were then assayed for alkaline phosphatase activity 72 hours after the addition of conditioned culture supernatant using a chemiluminescence procedure. Cellular alkaline phosphatase was extracted by washing the cells with PBS and cells were lysed with three cycles of freeze thaw in 100 µL/cm$^2$ of 25 mM Tris-HCL, pH 8.0 and Triton X-100. For detection of alkaline phosphatase 2 µL of CSPD® ready-to-use with Sapphire II enhancer (Tropix, Bedford, Mass.) in an eppendorf tube, vortexed and incubated at room temperature for 30 seconds. The light output from each sample was integrated for 10 seconds after a 2 second delay by a Glomax 20/20 luminometer. (Promega, Madison, Wis.). Alkaline phosphatase detection signal was recorded in relative luminescence units (RLU).

Critical Size Defect Model

The critical size defect was introduced into the rat fibula. Adult homozygous Athymic RNU Nude rats weighing (200-300 g) were administered buprenorphine at 2 mg/kg by subcutaneous injection into the right thigh one hour prior to surgery. The rats underwent general anesthesia through the use of an animal vaporizer that dispensed isoflurane at 2-4% initial induction and 1-2% throughout the surgery. Each animal was shaved, disinfected with Hibiclens and isolated to a sterile surgical field that included a surgical drape that allowed only the left hind limb to be exposed. A lateral incision in the skin of about 2 cm was performed on the lower leg, along with a smaller incision into the gastrocnemius muscle. This muscle was retracted in order to expose the fibula and an osteotomy was performed to create a 2-4 mm segmental defect on the diaphysis of the fibula. Cells were then introduced into the defect void by placement into a sutured muscle pocket. Animals (n=8) were euthanized and tissues isolated at various time points as indicated in the text. All animal studies were performed in accordance with the standards of Baylor College of Medicine, Department of Comparative Medicine, after review and approval of the protocol by the Institutional Animal Care and Use Committee (IACUC).

Radiographic Analysis of the New Bone

Hind limbs were harvested and radiographically analyzed using an XPERT model faxitron (Kubtec, Fairfield, Conn.) in biplanar projections. Samples were set at an exposure time of 15 seconds and acceleration voltage of 30 kV. Bone healing was evaluated with radiographs at the termination of each study. Qualitative radiographic analyses were performed using microcomputed tomography (MicroCT) system (eXplore Locus SP: GE Healthcare, London, ON, Canada) at 14 µm resolution. Bone density was determined with a density calibration phantom. Three-dimensional reconstructions and cross-sections of the hind limb were generated to identify the defect void and new bone.

Histological Analysis of the New Bone

Animals (n=8) were euthanized at weekly intervals starting at 2 weeks and ending at 12 weeks. Hind limbs were isolated; formalin fixed, and decalcified paraffin embedded. Serial sections (5 µm) were prepared that encompassed the critical defect site. Hematoxylin and eosin staining was performed on every fifth slide to locate the newly forming endochondral bone. All sections were analyzed by light microscopy.

Dose Response to AdBMP2 Transduced Cells

Since all defects introduced into the fibula were unable to heal, we next defined the dose of AdBMP2 transduced cells that is required to provide optimal healing of the bone defect. Rather than vary the concentration of virus particles per cell, which is difficult since virus infection follows the Poisson distribution rather than a linear model, we chose to vary the number of cells introduced in the model in order to provide a linear range in the amount of BMP2 produced. In these studies, fibroblasts were transduced with AdBMP2 at 2500 vp/cell and BMP2 protein and activity was quantified 72 hours later. Total BMP2 protein within the culture supernatant was approximately 18.6 nanograms per $1 \times 10^6$ cells which is significantly (p<0.0001) elevated over the amount of BMP2 produced in similar numbers of cells transduced with Adempty cassette or no adenovirus.

Further, BMP2 protein activity, as determined by the elevation in the BMP2 responsive protein alkaline phosphatase, showed that this BMP2 being made is active and is significantly elevated in comparison to either the cells transduced with AdEmpty cassette or cells alone (2B). Various numbers of the AdBMP2 transduced cells were next injected simultaneously with the introduction of a 3 mm bone defect in the fibula. The cells were injected into the void region, and surrounding muscle tissues of the rats (n=5), and potential bone formation allowed to progress for two weeks. The inventors observed that the new bone formation varied drastically with cell numbers. They did not observe any bone formation or healing in the samples receiving $5 \times 10^4$ cells, suggesting that there is a threshold amount of BMP2 required for inducing bone formation. Alternatively, there was no statistical difference between the two highest cell numbers or doses, indicating that there is a maximum bone formation response that can be achieved with this system. The data demonstrates that $5 \times 10^6$ cells provided a maximum response for the least number of AdBMP2 transduced cells.

The present invention further provides for bone healing using a minimal dose of $5 \times 10^6$ AdBMP2 transduced cells. This number of cells yields approximately 93 ngs of total BMP2 protein within culture supernatant over a three day period. Although lesser numbers of AdBMP2 transduced cells ($5 \times 10^5$) or BMP2 (9 ngs) did result in heterotopic bone formation, it was not enough to reliably heal the fibula defect and doses below this number (1 ng) were unable to induce heterotopic ossification. Delivery of additional cells beyond the $5 \times 10^6$ transduced cells resulted in a similar volume of bone, suggesting that there is an upper threshold at which perhaps all the BMP2 receptors are saturated and no additional response will occur. Further, the volume of bone obtained when 5×10$^6$ AdBMP2 transduced cells were delivered to the defect was larger than required for complete healing, and substantial resorption was observed within the first 2-4 weeks as the fibula regained is physiological shape.

The initial new bone was observed within 10 days of delivery, with the first emergence of a remodeled bone with cortical appearance and inner marrow cavity appearing at 6 weeks. At 9 weeks, all samples appeared to be well remodeled with visible contiguous cortical bone, suggesting that at this point, all defects were reliably healed. The inventors observed little change from 9 weeks to 12 weeks, although there was additional bone observed associated with the newly formed skeletal bone. The majority of the bone remodeling and resorption occurred within the first 4 weeks, where the callus like structure resorbs to start to form the shape of the fibula. The inventors did not observe additional resorption of the bone beyond 6 weeks, indicating that the new bone functions as skeletal bone and is maintained similar to the original fibula.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The following references and any cited in the preceding Disclosure are hereby incorporated by reference in their entireties and in particular for any content for which a reference is specifically cited.

[1] Deyo R, Nachemson A, Mirza S. Spinal-Fusion Surgery—The Case for Restraint. New England Journal of Medicine 2004; 350:722-6.

[2] Kimelman N, Pelled G, Helm G, et al. Review: Gene- and Stem Cell-Based Therapeutics for Bone Regeneration and Repair. Tissue Engineering 2007; 13:1135-50.

[3] Lutolf M, Weber F, Schmoekel H, et al. Repair of bone defects using synthetic mimetics of collagenous extracellular matrices. Nature Biotechnology 2003; 21:513-8.

[4] Mussano F, Ciccone G, Ceccarelli M, et al. Bone Morphogenetic Proteins and Bone Defects: A Systematic Review. Spine 2007; 32:824.

[5] Garrison K R, Donell S, Ryder J, et al. Clinical effectiveness and cost-effectiveness of bone morphogenetic proteins in the non-healing of fractures and spinal fusion: a systematic review. Health Technology Assessment 2007; 11:1-150, iii-iv.

[6] Hecht B P, Fischgrund J S, Herkowitz H N, et al. The use of recombinant human bone morphogenetic protein 2 (rhBMP-2) to promote spinal fusion in a nonhuman primate anterior interbody fusion model. Spine 1999; 24:629-36.

[7] Shore E M, Xu M, Feldman G J, et al. A recurrent mutation in the BMP type I receptor ACVR1 causes inherited and sporadic fibrodysplasia ossificans progressiva. Nature Genetics 2006; 38:525-7.

[8] Olmsted-Davis E A, Gugala Z, Gannon F H, et al. Use of a chimeric adenovirus vector enhances BMP2 production and bone formation. Human Gene Therapy 2002; 13:1337-47.

[9] Wang J C, Kanim L E A, Yoo S, et al. Effect of regional gene therapy with bone morphogenetic protein-2-producing bone marrow cells on spinal fusion in rats. The Journal of Bone and Joint Surgery 2003; 85:905.

[10] Alden T D, Pittman D D, Beres E J, et al. Percutaneous spinal fusion using bone morphogenetic protein-2 gene therapy. J Neurosurg 1999; 90:109-14.

[11] Miyazaki M, Sugiyama O, Zou J, et al. Comparison of lentiviral and adenoviral gene therapy for spinal fusion in rats. Spine 2008; 33:1410-7.

[12] Yoon S T, Boden S D. Spine fusion by gene therapy. Gene Ther 2004; 11:360-7.

[13] Fouletier-Dilling C M, Bosch P, Davis A R, et al. Novel compound enables high-level adenovirus transduction in the absence of an adenovirus-specific receptor. Hum Gene Ther 2005; 16:1287-97.

[14] Tomko R P, Xu R, Philipson L. HCAR and MCAR: the human and mouse cellular receptors for subgroup C adenoviruses and group B coxsackieviruses. Proc Natl Acad Sci USA 1997; 94:3352-6.

[15] Duncan S J, Gordon F C, Gregory D W, et al. Infection of mouse liver by human adenovirus type 5. J Gen Virol 1978; 40:45-61.

[16] Alden T D, Hankins G R, Beres E J, et al. Bone morphogenetic protein gene therapy for the induction of spinal arthrodesis. Neurosurg Focus 1998; 4:e12.

[17] Fouletier-Dilling C, Gannon F, Olmsted-Davis E, et al. Efficient and Rapid Osteoinduction in an Immune-Competent Host. Human Gene Therapy 2007; 18:733-45.

[18] Thies R. Recombinant human bone morphogenetic protein-2 induces osteoblastic differentiation in W-20-17 stromal cells. Endocrinology 1992; 130:1318-24.

[19] Davis A, Wivel N, Palladino J, et al. Construction of adenoviral vectors. Molecular Biotechnology 2001; 18:63-70.

[20] Olmsted E, Blum J, Rill D, et al. Adenovirus-Mediated BMP2 Expression in Human Bone Marrow Stromal Cells. Journal of Cellular Biochemistry 2001; 82:11-21.

[21] Hipp J, Reitman C, Wharton N. Defining Pseudoarthrosis in the Cervical Spine With Differing Motion Thresholds. Spine 2005; 30:209.

[22] Zhao K, Yang C, Zhao C, et al. Assessment of noninvasive intervertebral motion measurements in the lumbar spine. Journal of Biomechanics 2005; 38:1943-6.

[23] Olmsted-Davis E, Gannon F H, Ozen M, et al. Hypoxic adipocytes pattern early heterotopic bone formation. American Journal of Pathology 2007; 170:620-32.

[24] Hasharoni A, Zilberman Y, Turgeman G, et al. Murine spinal fusion induced by engineered mesenchymal stem cells that conditionally express bone morphogenetic protein-2. J Neurosurg Spine 2005; 3:47-52.

[25] Sheyn D, Pelled G, Zilberman Y, et al. Nonvirally engineered porcine adipose tissue-derived stem cells: use in posterior spinal fusion. Stem Cells 2008; 26:1056-64.

[26] Kimelman-Bleich N, Pelled G, Sheyn D, et al. The use of a synthetic oxygen carrier-enriched hydrogel to enhance mesenchymal stem cell-based bone formation in vivo. Biomaterials 2009; 30:4639-48.

[27] Sheyn D, Ruthemann M, Mizrahi O, et al. Genetically Modified Mesenchymal Stem Cells Induce Mechanically Stable Posterior Spine Fusion. Tissue Eng Part A.

[28] Gottfried O, Dailey A. Mesenchymal Stem Cell and Gene Therapies for Spinal Fusion. Topic Review. Neurosurgery 2008; 63:380-92.

[29] Aslan H, Sheyn D, Gazit D. Genetically engineered mesenchymal stem cells: applications in spine therapy. Regenerative Medicine 2009; 4:99-108.

[30] Weber F, Eyrich G, Gratz K, et al. Slow and continuous application of human recombinant bone morphogenetic protein via biodegradable poly(lactide-co-glycolide) foamspheres. International Journal of Oral & Maxillofacial Surgery 2002; 31:60-5.

[31] Windahl S, Andersson G, Gustafsson J. Elucidation of estrogen receptor function in bone with the use of mouse models. Trends in Endocrinology & Metabolism 2002; 13:195-200.

[32] Gugala Z, Olmsted-Davis E, Gannon F, et al. Osteoinduction by ex vivo adenovirus-mediated BMP2 delivery is independent of cell type. Gene Therapy 2003; 10:1289-96.

[33] Moutsatsos I K, Turgeman G, Zhou S, et al. Exogenously regulated stem cell-mediated gene therapy for bone regeneration. Molecular Therapy 2001; 3:449-61.

[34] Bollard C M, Gottschalk S, Leen A M, et al. Complete responses of relapsed lymphoma following genetic modification of tumor-antigen presenting cells and T-lymphocyte transfer. Blood 2007; 110:2838-45.

[35] Shafer J, Davis A R, Gannon F H, et al. Oxygen tension directs chondrogenic differentiation of myelo-monocytic progenitors during endochondral bone formation. Tissue Eng 2007; 13:2011-9.

[36] K. L. Berkner, Development of adenovirus vectors for the expression of heterologous genes, Biotechniques 6, 616 (July-August, 1988).

[37] Murugan, R. & Ramakrishna, S. Development of nanocomposites for bone grafting. Composites Science and Technology 65, 2385-2406 (2005).

[38] Srouji, S., Blumenfeld, I., Rachmiel, A. & Livne, E. Bone defect repair in rat tibia by TGF-1 and IGF-1 released from hydrogel scaffold. Cell and tissue banking 5, 223-230 (2004).

[39] Yoneda, M. et al. Repair of an intercalated long bone defect with a synthetic biodegradable bone-inducing implant. Biomaterials 26, 5145-5152 (2005).

[40] Mistry, A. & Mikos, A. Tissue engineering strategies for bone regeneration. Advances in Biochemical Engineering Biotechnology 94, 1-22 (2005).

[41] Bikram, M. et al. Endochondral Bone Formation from Hydrogel Carriers Loaded with BMP2-transduced Cells. Annals of Biomedical Engineering 35, 796-807 (2007).

[42] Bishop, G. B. & Einhorn, T. A. Current and future clinical applications of bone morphogenetic proteins in orthopaedic trauma surgery. Int Orthop 31, 721-727 (2007).

[43] Cahill, K. S., Chi, J. H., Day, A. & Claus, E. B. Prevalence, complications, and hospital charges associated with use of bone-morphogenetic proteins in spinal fusion procedures. JAMA 302, 58-66 (2009).

[44] Gautschi, O. P., Frey, S. P. & Zellweger, R. Bone morphogenetic proteins in clinical applications. ANZ Journal of Surgery 77, 626-631 (2007).

[45] Jung, R. E. et al. A randomized-controlled clinical trial evaluating clinical and radiological outcomes after 3 and 5 years of dental implants placed in bone regenerated by means of GBR techniques with or without the addition of BMP-2. Clinical Oral Implants Research 20, 660-666 (2009).

[46] Liu, Y., Hunziker, E., Vaal, C. & Groot, K. Biomimetic Coatings vs. Collagen Sponges as a Carrier for BMP-2: A Comparison of the Osteogenic Responses Triggered in vivo Using an Ectopic Rat Model. Key Engineering Materials 254, 619-622 (2004).

[47] Schmoekel, H. et al. Bone repair with a form of BMP-2 engineered for incorporation into fibrin cell ingrowth matrices. Biotechnology and Bioengineering 89, 253-262 (2005).

[48] Weber, F., Eyrich, G., Gratz, K., Maly, F. & Sailer, H. Slow and continuous application of human recombinant bone morphogenetic protein via biodegradable poly(lactide-co-glycolide) foamspheres. International Journal of Oral & Maxillofacial Surgery 31, 60-65 (2002).

[49] Halstenberg, S., Panitch, A., Rizzi, S., Hall, H. & Hubbell, J. Biologically engineered protein-graft-poly(ethylene glycol) hydrogels: a cell adhesive and plasmin-degradable biosynthetic material for tissue repair. Biomacromolecules 3, 710-723 (2002).

[50] Peppas, N. A. in Biomaterials Science: An Introduction to Materials in Medicine. (ed. A. S. H. B. D. Ratner, F. J. Schoen and J. E. Lemons) 100-107 (Elsevier Academic Press, San Diego; 2004).

[51] Tsang, V. et al. Fabrication of 3D hepatic tissues by additive photopatterning of cellular hydrogels. The FASEB Journal 21, 790 (2007).

[52] Fouletier-Dilling, C. et al. Efficient and Rapid Osteoinduction in an Immune-Competent Host. Human Gene Therapy 18, 733-745 (2007).

[53] Thies, R. Recombinant human bone morphogenetic protein-2 induces osteoblastic differentiation in W-20-17 stromal cells. Endocrinology 130, 1318-1324 (1992).

[54] Price C T, Connolly J F, Carantzas A C, et al. Comparison of bone grafts for posterior spinal fusion in adolescent idiopathic scoliosis. Spine (Phila Pa. 1976) 2003; 28:793-8.

[55] Goldberg V M. Selection of bone grafts for revision total hip arthroplasty. Clin Orthop Relat Res 2000:68-76.

[56] Nishida J, Shimamura T. Methods of reconstruction for bone defect after tumor excision: a review of alternatives. Med Sci Monit 2008; 14:RA107-13.

[57] Malizos K N, Zalavras C G, Soucacos P N, et al. Free vascularized fibular grafts for reconstruction of skeletal defects. J Am Acad Orthop Surg 2004; 12:360-9.

[58] Cornell C N. Osteobiologics. Bull Hosp Jt Dis 2004; 62:13-7.

[59] Hill P A. Bone remodelling. Br J Orthod 1998; 25:101-7.

[60] Vaananen H K, Zhao H, Mulari M, et al. The cell biology of osteoclast function. J Cell Sci 2000; 113 (Pt 3):377-81.

[61] Lecaille F, Bromme D, Lalmanach G. Biochemical properties and regulation of cathepsin K activity. Biochimie 2008; 90:208-26.

[62] Nosaka A Y, Kanaori K, Teno N, et al. Conformational studies on the specific cleavage site of Type I collagen (alpha-1) fragment (157-192) by cathepsins K and L by proton NMR spectroscopy. Bioorg Med Chem 1999; 7:375-9.

[63] Hahn M S, Taite L J, Moon J J, et al. Photolithographic patterning of polyethylene glycol hydrogels. Biomaterials 2006; 27:2519-24.

[64] Collin-Osdoby P, Yu X, Zheng H, et al. RANKL-mediated osteoclast formation from murine RAW 264.7 cells. Methods Mol Med 2003; 80:153-66.

[65] Cruise G M, Hegre O D, Lamberti F V, et al. In vitro and in vivo performance of porcine islets encapsulated in interfacially photopolymerized poly(ethylene glycol) diacrylate membranes. Cell transplantation 1999; 8:293-306.

What is claimed is:

1. A method to induce bone formation in a mammal, said method
comprising the step of:
delivering to a targeted site of a mammal one or more cells transduced with a virus containing nucleic acids encoding a bone morphogenetic protein, said one or more transduced cells encapsulated in at least one poly(ethylene glycol) diacrylate (PEG-DA) hydrogel microsphere, wherein said at least one hydrogel microsphere contains up to 100 of said transduced cells, wherein said at least one hydrogel microsphere is formed by
forming a hydrogel precursor solution by combining PEG-DA with triethanolamine/HEPES buffered saline, 1-vinyl-2-pyrrolidinone, eosin Y, and said one or more transduced cells;
forming a mineral oil solution by combining acetophenone, 1-vinyl-2-pyrrolidinone, and mineral oil;
combining said hydrogel precursor solution with said mineral oil solution; and
emulsifying said combined solution.

2. The method of claim 1 wherein the one or more cells are configured to produce bone morphogenetic protein-2 by transducing said one or more cells with at least one viral vector having nucleic acids encoding a human bone morphogenetic protein-2.

3. The method of claim 1 wherein said one or more transduced cells encapsulated in said at least one microsphere are delivered to the bone defect via a syringe.

4. The method of claim 1 wherein a plurality of said hydrogel microspheres containing said transduced cells are injected into said mammal and wherein said plurality of microspheres have an average radii of about 50 μm-150 μm.

5. The method of claim 1 wherein said delivery is configured to form bone of desired size and shape at the targeted location.

6. The method of claim 1 wherein the at least one hydrogel microsphere is degradable by at least one enzyme in the body of the individual.

7. A method to induce bone formation in a mammal, said method comprising the step of:
delivering to a targeted site of a mammal one or more cells transduced with a virus containing nucleic acids encoding a bone morphogenetic protein, said one or more transduced cells encapsulated in at least one poly(ethylene glycol) (PEG) hydrogel microsphere, wherein said at least one hydrogel microsphere contains up to 100 of said transduced cells.

8. The method of claim 7 wherein the at least one PEG hydrogel microsphere is degradable by at least one protease produced by osteoblasts.

* * * * *